United States Patent
Deno et al.

(10) Patent No.: US 7,142,916 B2
(45) Date of Patent: Nov. 28, 2006

(54) CARDIAC PACING MODALITY HAVING IMPROVED BLANKING, TIMING, AND THERAPY DELIVERY METHODS FOR EXTRA-SYSTOLIC STIMULATION PACING THERAPY

(75) Inventors: D. Curtis Deno, Andover, MN (US); Vincent E. Splett, Apple Valley, MN (US); Jeffrey M. Gillberg, Coon Rapids, MN (US); Glenn C. Zillmer, Hudson, WI (US); Ruth N. Klepfer, St. Louis Park, MN (US); Karen J. Kleckner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 473 days.

(21) Appl. No.: 10/692,990

(22) Filed: Oct. 24, 2003

(65) Prior Publication Data

US 2005/0090872 A1   Apr. 28, 2005

(51) Int. Cl.
*A61N 1/36* (2006.01)
(52) U.S. Cl. .................................................. 607/9
(58) Field of Classification Search .............. 600/16; 607/9, 11, 14, 15, 25
See application file for complete search history.

(56) References Cited

U.S. PATENT DOCUMENTS 5,213,098 A    5/1993   Bennett et al.
6,438,408 B1 *  8/2002   Mulligan et al. ........... 600/510
2004/0220631 A1 * 11/2004   Burnes et al. .................. 607/9
2004/0220640 A1 * 11/2004   Burnes et al. ................ 607/28

FOREIGN PATENT DOCUMENTS

| WO | WO 01/58518 | 8/2001 |
|---|---|---|
| WO | WO 02/053026 | 7/2002 |
| WO | WO03020364 | 3/2003 |

* cited by examiner

*Primary Examiner*—Robert E. Pezzuto
*Assistant Examiner*—Terri Lynn Smith
(74) *Attorney, Agent, or Firm*—Paul H. McDowall; Girma Wolde-Michael

(57) ABSTRACT

The present invention relates to the secure delivery of an extra-systolic stimulation (ESS) therapy to treat cardiac dysfunction that employs atrial and/or ventricular extra-systoles via pacing-like stimulation of the heart. These extra-systoles must be timed correctly to achieve beneficial effects on myocardial mechanics (benefit) while maintaining an extremely low level of risk of arrhythmia induction and excellent ICD-like arrhythmia sensing and detection (security). Further experience with ESS has led to improved implementation methods that depend on better blanking, ESS stimulation timing (of an "extra-systolic interval" or ESI), and ESS therapy delivery options and guidance. These methods may be employed individually or in combinations in an external or implantable ESS therapy delivery device.

44 Claims, 14 Drawing Sheets

Optimal ESI Timing and Heart Rate

- Sweet spot, balancing safety and effect, narrows and moves closer to refractory period as rate increases
- Upper rate limit necessary for CPT
- Adjustment of ESI with rate not necessarily identical to refractory or QT interval change with rate, depending on strategy and upper rate limit
- Importance of tracking refractory period

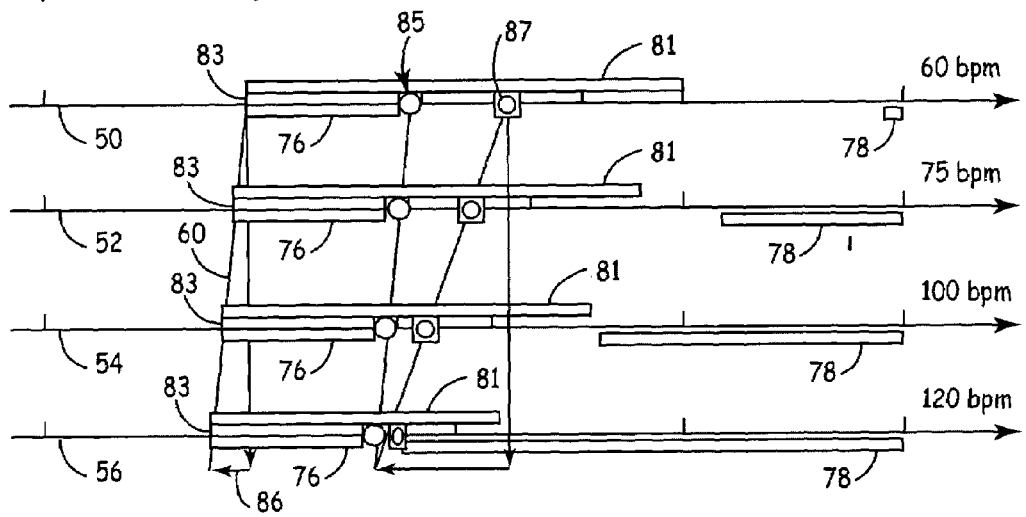

- ▣ Optimally robust spot (87)
- ▭ Excess risk: induced VT/VF (76)
- ▭ Excess risk: paced Vcp tach (78)
- ○ Maximal benefit at fixed acceptable risk spot (85)
- ▭ Benefit: hemodynamic, exercise capacity (81)
- ▭ Benefit: rate lowering, reverse remodeling (83)

FIG. 5

FIG. 6
Longest Undetectable Interval (= ESI + 150ms)
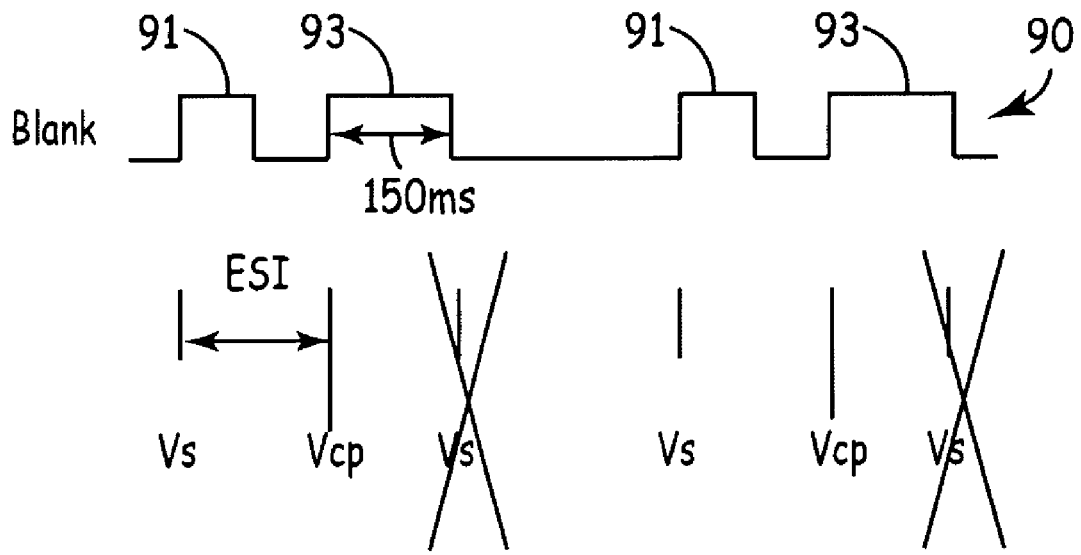
Shortest Undetectable Interval (= ESI)
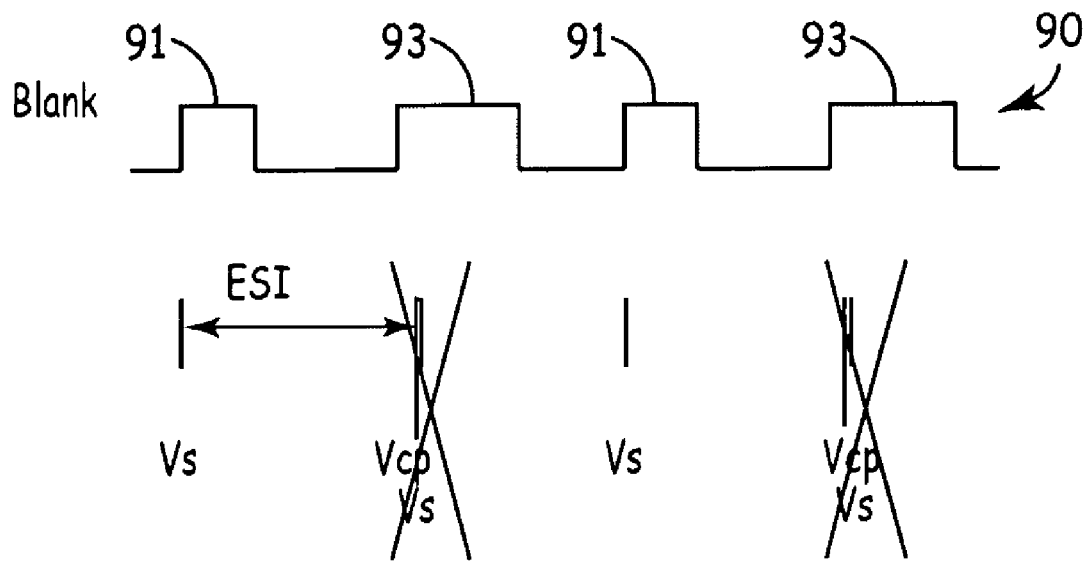

FIG. 7

Proposed Solutions

- Periodically drop ESS
  - Implementation of M of M+1 reveals VT after median delay of M/2 ESS cycles
  - Investigate reducing M at higher rates
  - Consider M = infinity (always on) if rate low enough. (m=0, always off, is already achieved at high rates via ESS rate limit safety rule.)
  - Can speed detection of VTs that are not 2:1 but are close and start with a phase that would otherwise delay their detection
- Suspend ESS upon inappropriate Asense timing
  - Safety rule engages with loss of AV synchrony during most VTs
- Dither timing of A-A or A-V intervals though A or V pacing
  - Occasional variations of 50-100 ms either way (if blanking is short) may be sufficient to enable hidden VT detection
- Auxiliary sensing vector
  - Use Coil-to-Can or other low polarization EGM signals to detect Vsense in blanking window
  - Discriminate by time or morphology from expected CPT evoked response
- Look for rate Irregularity as a clue to hidden VT
  - As VT rate enters/leaves undetectable VT zone, CPT rate will abruptly halve/double (perhaps exceeding upper rate limit)
- Reduce blanking/refractory
  - Moves left hand limit to the right (see diagram)
  - Incomplete solution by itself, since Vcp is intended to cause a prompt depolarization which needs to be blanked
  - Perhaps complete solution if implement electronic blanking of known time/morphology evoked R waves but not VTs (see auxiliary sensing vector note)
  - Two fold increase of change of R-R interval at base mechanical rate per change of blanking significantly adds to heart rate range over which VTs can be detected without dropping ESS beats
  - In principle, atrial cross chamber blanking can be made short enough (a few ms) to never hide a VT
  - Could be accomplished with low polarization leads or sense amp electronics modifications.
  - May be combined with auxiliary sensing vector solution
- Deliver ESS with short ESI
  - Enhances window for VT detection (particularly at a low ESS rates)
- Keep ESS upper rate limit low
  - Caps aliased VT rates. Upper limit 75 bpm makes all VTs faster than nominal VTDI detectable
  - Exploit in conjunction with reducing blanking and short ESIs (see above) to be least restrictive
  - Use an appropriately lower rate limit if Vpacing and not Vsensing to account for propagation differences.

VT Detection and Operating Range (to 70 bpm)

Transient Override of Rate Limit to Permit Mediated Rate Reduction

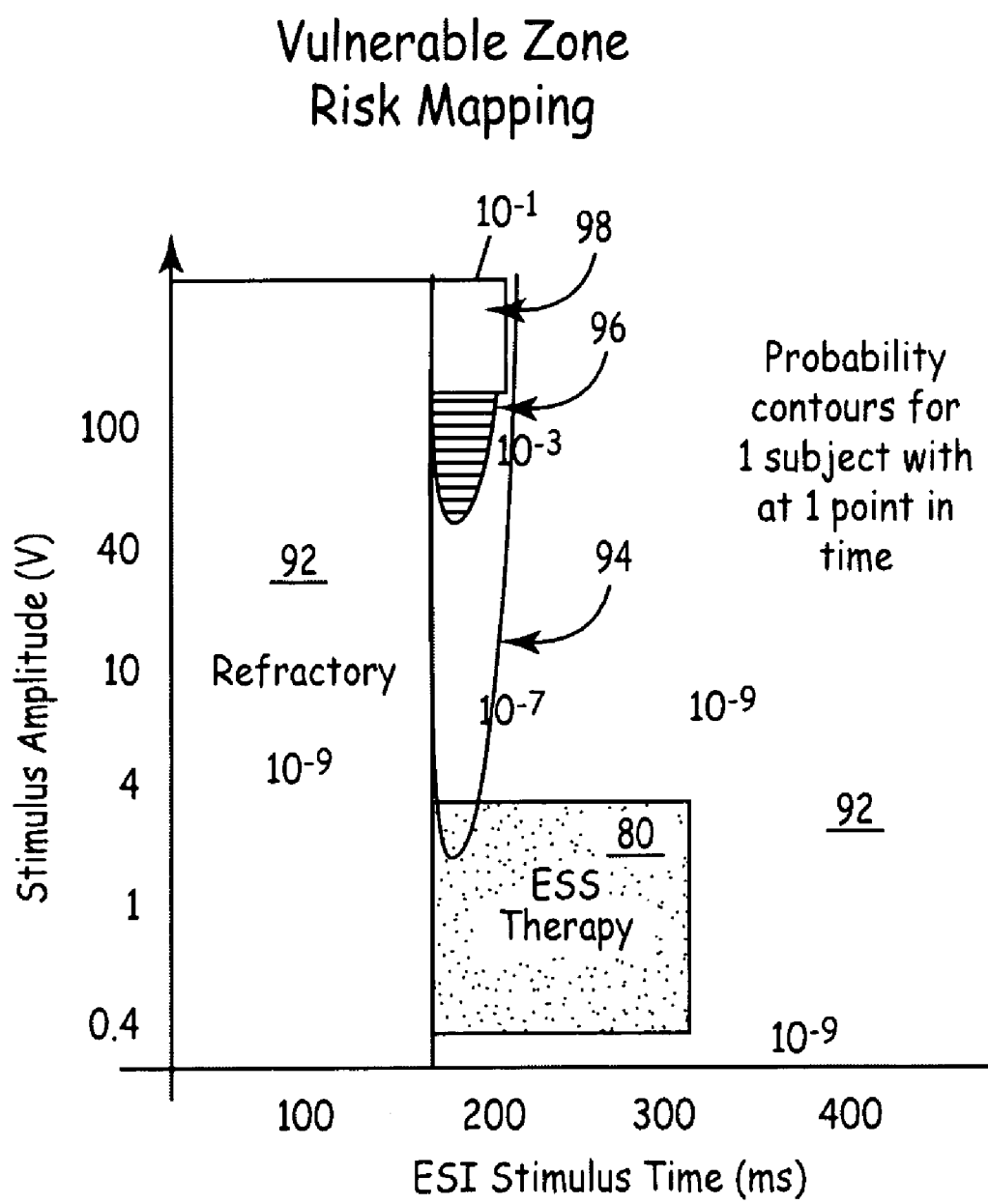

CARDIAC PACING MODALITY HAVING IMPROVED BLANKING, TIMING, AND THERAPY DELIVERY METHODS FOR EXTRA-SYSTOLIC STIMULATION PACING THERAPY

CROSS REFERENCE TO RELATED APPLICATIONS

The present non-provisional patent application claims the benefit of provisional patent application Ser. No. 60/509204 entitled, "CARDIAC PACING MODALITY HAVING IMPROVED BLANKING, TIMING, AND THERAPY DELIVERY METHODS FOR EXTRA-SYSTOLIC STIMULATION PACING THERAPY," filed 7 Oct. 2003 and hereby cross-references and incorporates by reference the entire contents of the following applications, each of which was filed on 7 Oct. 2003: non-provisional U.S. application Ser. No. 10/680528 entitled, "REFRACTORY PERIOD TRACKING AND ARRHYTHMIA DETECTION," non-provisional U.S. application Ser. No. 10/680462 entitled, "METHOD AND APPARATUS FOR CONTROLLING EXTRA-SYSTOLIC STIMULATION (ESS) THERAPY USING ISCHEMIA DETECTION," non-provisional U.S. application Ser. No. 10/680494 entitled, "METHOD AND APPARATUS FOR OPTIMIZATION AND ASSESSMENT OF RESPONSE TO EXTRA-SYSTOLIC STIMULATION (ESS) THERAPY," non-provisional U.S. application Ser. No. 10/680493 entitled, "EXTRA-SYSTOLIC STIMULATION THERAPY DELIVERY AND SENSING VIA DIFFERENT ELECTRODE SETS," non-provisional U.S. application Ser. No. 10/680695 entitled, "MULTIPLE PACING OUTPUT CHANNELS," and provisional U.S. application Ser. No. 60/509335 entitled, "SECURE AND EFFICACIOUS THERAPY DELIVERY FOR AN EXTRA-SYSTOLIC STIMULATION PACING ENGINE."

FIELD OF THE INVENTION

The present invention relates generally to the field of cardiac stimulation devices and more specifically to a device and method for secure and efficacious delivery of an extra-systolic stimulation (ESS) therapy to improve hemodynamic function in the treatment of cardiac mechanical insufficiency. In particular, implantable and external devices and methods of therapy delivery according to the present invention are provided for measuring myocardial electrical restitution and adjusting the timing of extra-systolic stimulation based on the electrical restitution measurement.

BACKGROUND OF THE INVENTION

Cardiac myocytes stimulated with so-called paired, coupled, bi-geminal or intercalated pacing stimulation produce enhanced mechanical function on subsequent depolarizations of the heart. Herein, this type of cardiac pacing therapy is referred to as extra-systolic stimulation (ESS) which refers to delivery of cardiac pacing therapy soon after either an intrinsic or pacing-induced systole. The magnitude of the enhanced mechanical function is particularly dependent on the timing of the extra systole relative to the preceding intrinsic or paced systole. When correctly timed, an ESS pulse causes depolarization of the heart but the attendant mechanical contraction is absent or substantially weakened. The contractility of the subsequent cardiac cycles, referred to as the post-extra-systolic beats, is increased as described in detail in commonly assigned U.S. Pat. No. 5,213,098 issued to Bennett et al., incorporated herein by reference in its entirety.

The mechanism of ESS is thought to be related to the calcium cycling within the myocytes. The extra systole initiates a limited calcium release from the sarcolasmic reticulum (SR). The limited amount of calcium that is released in response to the extra systole is not enough to cause a normal mechanical contraction of the heart. After the extra systole, the SR continues to take up calcium with the result that subsequent depolarization(s) cause a large release of calcium from the SR, resulting in vigorous myocyte contraction.

As noted, the degree of mechanical augmentation on post-extra-systolic beats depends strongly on the timing of the extra systole following a first depolarization, referred to as the extra-systolic interval (ESI). If the ESI is too long, the ESS effects are not achieved because a normal mechanical contraction takes place in response to the extra-systolic stimulus. As the ESI is shortened, maximal stroke volume effect, among others, occurs when the ESI is slightly longer than the physiologic refractory period. An electrical depolarization occurs without a mechanical contraction or with a substantially weakened added contraction. When the ESI becomes too short, the stimulus falls within the absolute refractory period and no depolarization occurs.

The above-cited Bennett patent generally discloses a post-extra-systolic potentiation stimulator for the treatment of congestive heart failure or other cardiac dysfunctions. A cardiac performance index is developed from a sensor employed to monitor the performance of the heart, and a cardiac stress index is developed from a sensor employed to monitor the cardiac muscle stress. Either or both the cardiac performance index and cardiac stress index may be used in controlling the delivery of ESS stimulation. Prior non-provisional U.S. patent application Ser. No. 10/322,792 filed 28 Aug. 2002 and corresponding PCT application (publication no. WO 02/053026) by to Deno et al., which is hereby incorporated herein by reference in its entirety, discloses an implantable medical device for delivering post extra-systolic potentiation stimulation. ESS stimulation is employed to strengthen the cardiac contraction when one or more parameters indicative of the state of heart failure show that the heart condition has progressed to benefit from increased contractility, decreased relaxation time, and increased cardiac output. PCT Publication WO 01/58518 by Darwish et al., incorporated herein by reference in its entirety, generally discloses an electrical cardiac stimulator for improving the performance of the heart by applying paired pulses to a plurality of ventricular sites. Multi-site paired pacing is proposed to increase stroke work without increasing oxygen consumption and, by synchronizing the timing of the electrical activity at a plurality of sites in the heart, decrease a likelihood of development of arrhythmia.

As indicated in the referenced '098 patent, one risk associated with ESS stimulation is arrhythmia induction. If the extra-systolic pulse is delivered to cardiac cells during the vulnerable period, the risk of inducing tachycardia or fibrillation in arrhythmia-prone patients is high. The vulnerable period encompasses the repolarization phase of the action potential, also referred to herein as the "recovery phase" and a period immediately following it. During the vulnerable period, the cardiac cell membrane is transiently hyper-excitable. Therefore, although the property of ESS has been known of for decades, the application of ESS in a cardiac stimulation therapy for improving the mechanical function of the heart has not been realized clinically because of the perceived risks.

In delivering extra-systolic stimulation for achieving mechanical enhancement of cardiac function on post-extra-systolic beats, therefore, it is important to avoid extra-systolic intervals that produce exaggerated shortening of the action potential duration and increased dispersion of the action potential duration and refractoriness. When securely delivered, the mechanical effects of ESS may advantageously benefit a large number of patients suffering from cardiac mechanical insufficiency, such as patients in heart failure. Hence, a method for controlling the timing of the extra-systolic stimuli during extra-systolic stimulation is needed that avoids increased risk of arrhythmias while providing desired beneficial effects of ESS therapy.

SUMMARY OF THE INVENTION

Extra-systolic stimulation (ESS) is a new means to treat cardiac dysfunction including heart failure that employs atrial and/or ventricular extrasystoles via pacing-like stimulation of the heart. These extrasystoles must be timed correctly to achieve beneficial effects on myocardial mechanics (benefit) while maintaining an extremely low level of risk of arrhythmia induction and excellent ICD-like arrhythmia sensing and detection (security). This timing must adapt to variations in refractory period such as those resulting from intrinsic or physiologic rate changes and not compromise security or benefit. Further experience with ESS has led to improved implementation methods that depend on better blanking, ESS stimulation timing, and ESS therapy delivery guidance. These methods may be employed individually or in combinations in an external or implantable ESS device. An exemplary list of these improvements appears below.

The present invention pertains to a series of prioritized therapy delivery guidance for delivery of an ESS therapy. According to the present invention, cardiac activity is monitored on a periodic (e.g., cycle-by-cycle) basis during delivery of ESS therapy and, based on current cardiac activity, a determination is made whether or not ESS therapy delivery should commence or continue (with or without changes to the therapy delivery regime).

For example, therapy delivery would be inhibited in the event that a premature beat (or depolarization) occurs such a premature atrial contraction (PAC) or a premature ventricular contraction (PVC).

In addition, the present invention maintains adequate arrhythmia detection and in the event that detection occurs, delivery of an ESS therapy is inhibited. Maintaining robust detection of ventricular tachycardia (VT) and ventricular fibrillation (VF) is deemed a prerequisite for secure and efficacious delivery of an ESS therapy.

By example and without limitation, representative therapy delivery options according to the present invention include:

Decision to withhold ESS therapy at rates and ESI intervals that are not compatible with the desired security and benefit profiles established by empiric rate based guidance for refractory period changes with rate (and/or by measurements to establish the refractory period such as from evoked R wave response/timing/morphology or T wave timing/morphology or ventricular pressure signal changes).

Linkage of Vcp ventricular ESS therapy stimulation pulse amplitude (or duration) to ESI and/or rate such that the risk of VTN induction is kept low, even at high rates where ESI is necessarily closer to the refractory period boundary.

Reducing ESI (extra-systolic interval, a key ESS therapy timing parameter) as rate increases (and conversely increase ESI with low rates) to maintain a security timing margin from the vulnerable zone, maintain a desired degree of potentiation, improve arrhythmia detection, and avoid diastolic compromise.

Testing if the rate dependent ESI above is compatible with a possible hidden VT and if so, either instituting the periodic withholding of ESS therapy or creating a further ESI decrease.

Reduced electrogram blanking times, cross chamber and same chamber, to extend arrhythmia sensing intervals and permit secure ESS therapy operation at higher heart rates.

Intermittently dropping ESS therapy application for one (or more) cardiac cycles every N cardiac cycles to expose hidden/aliased VT rhythms.

Delivering ESS therapy every cardiac cycle at rates sufficiently low there is no risk of a hidden VT and instituting a rate dependent rule for dropping ESS therapy application.

Incorporation of a brief alteration of rate (e.g. increase or decrease atrial rate using pacing) or AV interval when ESS therapy is operating near the boundary of a region of hidden/aliased VT) to test for a characteristic pattern of rate halving or doubling indicative of ongoing VT requiring termination of ESS therapy for arrhythmia treatment.

Situational (hysteresis) guidance for the initiation and suspension of ESS therapy stimulation based on heart rate and heart rate changes (or evoked R wave, T wave, or ventricular pressure characteristics or changes in those characteristics) that briefly allow ESIs that are long relative to cardiac cycle length at the onset of ESS therapy, and that become less so as heart rate falls with potentiation. Conversely, ESS therapy may not be suspended immediately upon slightly exceeding a rate limit established for long term use.

A reduction of the responsiveness to activity (rate response slope) in chronotropically incompetent patients during application of ESS therapy to reflect the enhanced functional state at a variety of rates and a reduced role for rate in cardiac reserve during ESS therapy.

The present invention provides a system and method for securely controlling the delivery of ESS therapy to effectively produce augmented stroke volume and the like in the therapeutic regime for cardiac mechanical insufficiency, among other afflictions.

According to the present invention, an ESS therapy may be delivered and controlled on a cycle-to-cycle basis. As such, the system includes an implantable medical device and associated lead system for delivering electrical stimulation pulses to the heart and receiving and processing electrical cardiac signals from the heart. The system includes arrhythmia detection and pacing therapy delivery capabilities and optionally, cardioversion and defibrillation capabilities. In some embodiments, the system further includes one or more physiological sensors for measuring cardiac hemodynamic or contractile function in order to assess the strength of the myocardial contraction during extra systoles and/or during depolarizations subsequent to delivery of ESS therapy.

BRIEF DESCRIPTION OF THE DRAWINGS

FIG. 5 schematically depicts possible risks and benefits for various ESI settings for several heart rates (i.e., 60, 75, 100 and 120 bpm).

FIG. 6 illustrates the longest and shortest ventricular arrhythmia detection window during ESS therapy delivery and includes a listing of a few relevant concerns and factors regarding arrhythmia detection during ESS therapy delivery.

FIG. 7 is a bullet list of some proposals to improve arrhythmia detection for an ESS therapy delivery regime.

FIG. 12 is a graphical depiction of vulnerable zone arrhythmia risk using the relationship between a range of ESS voltage amplitudes and ESI (in ms) with an ESS therapy delivery regions and several probability contours superimposed thereon.

DETAILED DESCRIPTION OF THE INVENTION

The present invention is directed toward providing an implantable system for securely and effectively delivering an electrical stimulation therapy to achieve augmented stroke volume by providing a carefully timed pacing stimulus to a chamber of a heart following an intrinsic or evoked depolarization. Herein the therapy is referred to as extra-systolic stimulation (ESS) therapy.

Figure 1A:
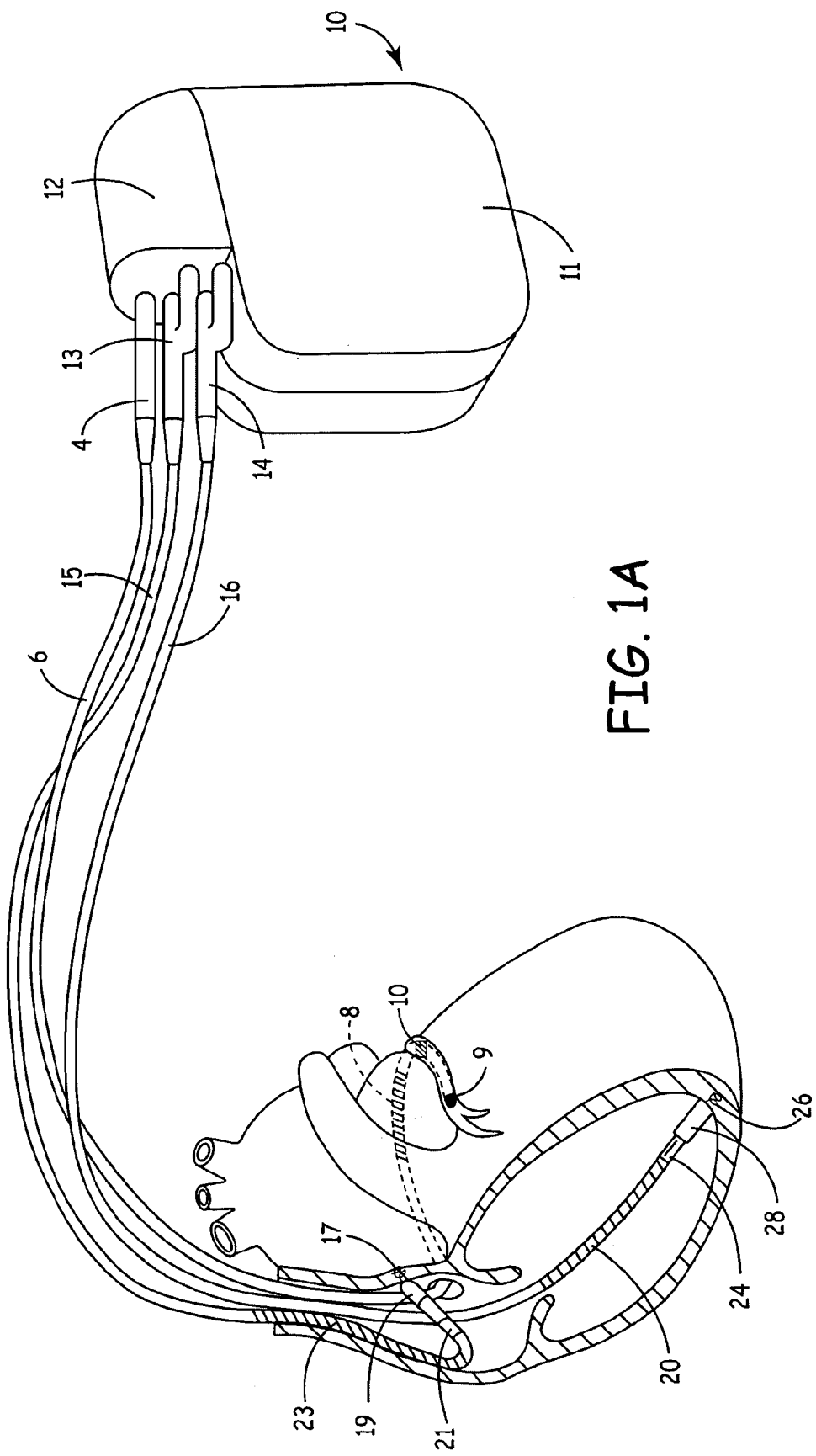
FIG. 1A is an illustration of an exemplary implantable medical device (IMD) in which the present invention may be implemented.

FIG. 1A is an illustration of an exemplary implantable medical device (IMD) in which the present invention may be implemented. IMD 10 is coupled to a patient's heart by three cardiac leads 6, 15, 16. IMD 10 is capable of receiving and processing cardiac electrical signals and delivering electrical stimulation pulses for ESS therapy and may additionally be capable of cardiac pacing, cardioversion and defibrillation. IMD 10 includes a connector block 12 for receiving the proximal end of a right ventricular lead 16, a right atrial lead 15 and a coronary sinus lead 6, used for positioning electrodes for sensing and stimulating in three or four heart chambers.

In FIG. 1A, the right ventricular lead 16 is positioned such that its distal end is in the right ventricle for sensing right ventricular cardiac signals and delivering electrical stimulation therapies in the right ventricle which includes at least ESS and may include cardiac bradycardia pacing, cardiac resynchronization therapy, cardioversion and/or defibrillation. For these purposes, right ventricular lead 16 is equipped with a ring electrode 24, a tip electrode 26 optionally mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to IMD 10.

The right atrial lead 15 is positioned such that its distal end is in the vicinity of the right atrium and the superior vena cava. Lead 15 is equipped with a ring electrode 21, a tip electrode 17, optionally mounted retractably within electrode head 19, and a coil electrode 23 for providing sensing and electrical stimulation therapies in the right atrium, which may include atrial ESS and/or other cardiac pacing therapies, cardioversion and/or defibrillation therapies. In one application of ESS, ESS therapy is delivered to the atria to improve the atrial contribution to ventricular filling. The extra-systolic depolarization resulting from the atrial ESS stimulation pulse may be conducted to the ventricles for achieving ESS effects in both the atrial and ventricular chambers. The ring electrode 21, the tip electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1A as having a defibrillation coil electrode 8 that may be used in combination with either the coil electrode 20 or the coil electrode 23 for delivering electrical shocks for cardioversion and defibrillation therapies. Coronary sinus lead 6 is also equipped with a distal tip electrode 9 and ring electrode 7 for sensing functions and delivering ESS in the left ventricle of the heart as well as other cardiac pacing therapies. The coil electrode 8, tip electrode 9 and ring electrode 7 are each coupled to insulated conductors within the body of lead 6, which provides connection to the proximal bifurcated connector 4. In alternative embodiments, lead 6 may additionally include ring electrodes positioned for left atrial sensing and stimulation functions, which may include atrial ESS and/or other cardiac pacing therapies.

The electrodes 17 and 21, 24 and 26, and 7 and 9 may be used in sensing and stimulation as bipolar pairs, commonly referred to as a "tip-to-ring" configuration, or individually in a unipolar configuration with the device housing 11 serving as the indifferent electrode, commonly referred to as the "can" or "case" electrode. IMD 10 is preferably capable of delivering high-voltage cardioversion and defibrillation therapies. As such, device housing 11 may also serve as a subcutaneous defibrillation electrode in combination with one or more of the defibrillation coil electrodes 8, 20, 23 for defibrillation of the atria or ventricles.

It is recognized that alternate lead systems may be substituted for the three lead system illustrated in FIG. 1A. For example, lead systems including one or more unipolar, bipolar and/or multi-polar leads may be configured for sensing cardiac electrical signals for delivering ESS. It is contemplated that extra-systolic stimuli may be delivered at one or more sites within the heart. Accordingly, lead systems may be adapted for sensing cardiac electrical signals for measuring restitution at multiple cardiac sites and for delivering extra-systolic stimuli at the multiple sites, which may be located in one or more heart chambers. It is further contemplated that subcutaneous ECG electrodes could be included in the implantable system.

Figure 1B:
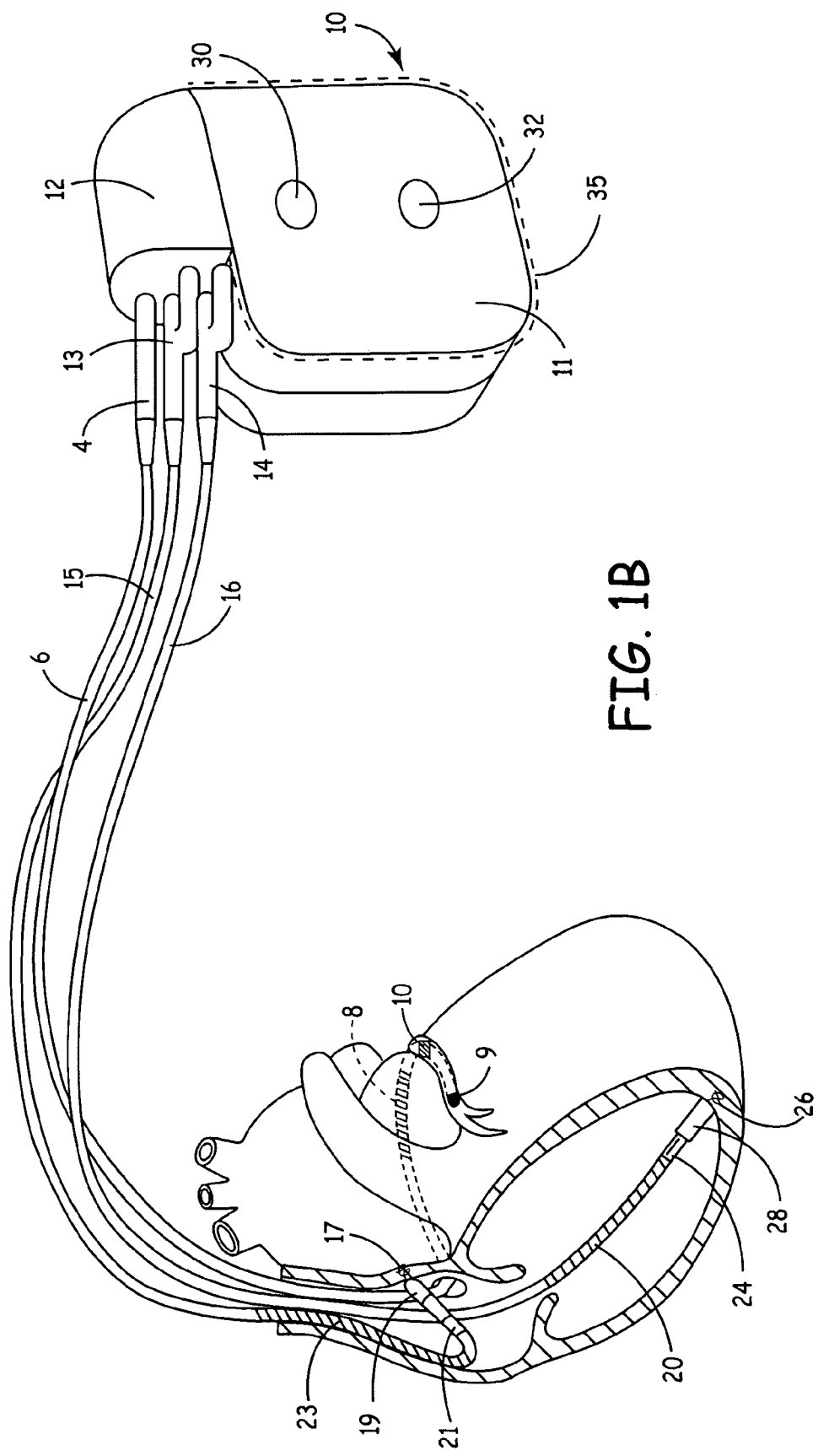
FIG. 1B is an illustration of an alternative IMD including subcutaneous ECG electrodes incorporated in the housing of the IMD.

FIG. 1B is an illustration of an alternative IMD coupled to a set of leads implanted in a patient's heart. In FIG. 1B, IMD housing 11 is provided with an insulative coating 35, covering at least a portion of housing 11, with openings 30,32. The uninsulated openings 30,32 serve as subcutaneous electrodes for sensing global ECG signals, which may be used in accordance with the present invention. An implantable system having electrodes for subcutaneous measurement of an ECG is generally disclosed in commonly assigned U.S. Pat. No. 5,987,352 issued to Klein, incorporated herein by reference in its entirety. In alternative embodiments, multiple subcutaneous electrodes incorporated on the device housing 11 and/or positioned on subcutaneous leads extending from IMD 10 may be used to acquire multiple subcutaneous ECG sensing vectors for measurement of electrical restitution. Multi-electrode ECG sensing in an implantable monitor is described in U.S. Pat. No. 5,313,953 issued to Yomtov, et al., incorporated herein by reference in its entirety.

While a particular multi-chamber IMD and lead system is illustrated in FIGS. 1A and 1B, methodologies included in the present invention may be adapted for use with other single chamber, dual chamber, or multichamber IMDs that are capable of sensing and processing cardiac electrical signals and delivering electrical stimulation pulses at controlled time intervals relative to an intrinsic or paced heart rate. Such IMDs optionally include other electrical stimulation therapy delivery capabilities such as bradycardia pacing, cardiac resynchronization therapy, anti-tachycardia pacing, and preferably include arrhythmia detection and cardioversion, and/or defibrillation capabilities.

Figure 2A:
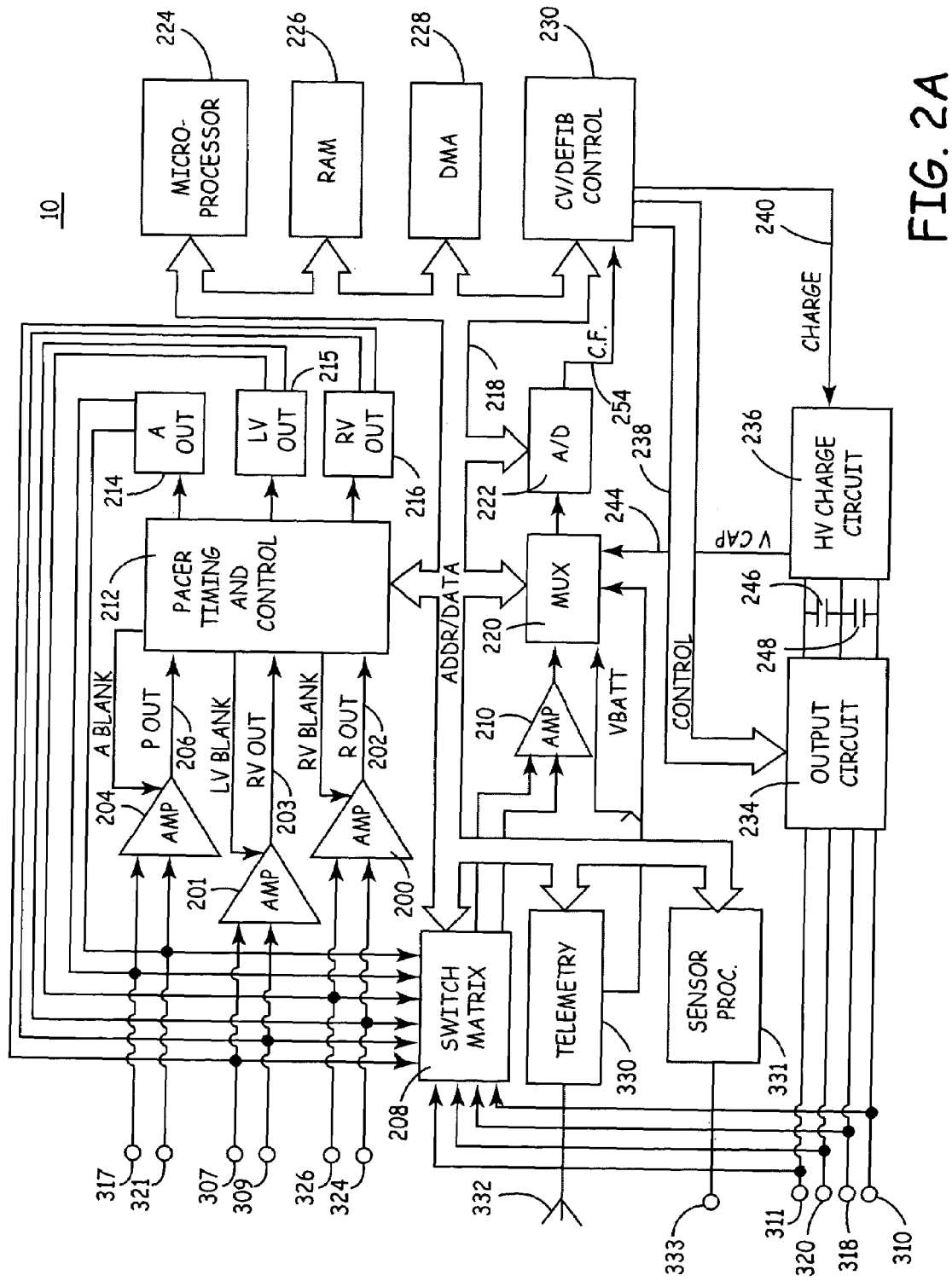
FIG. 2A is a functional schematic diagram of the implantable medical device shown in FIG. 1A.

A functional schematic diagram of the IMD 10 is shown in FIG. 2A. This diagram should be taken as exemplary of the type of device in which the invention may be embodied and not as limiting. The disclosed embodiment shown in FIG. 2A is a microprocessor-controlled device, but the methods of the present invention may also be practiced in other types of devices such as those employing dedicated digital circuitry. As such, the inventive methods according to the present invention include computer readable media coded with computer readable and executable instructions for carrying out said methods. Also, for physiologic therapy delivery data and discrete timing information used and/or temporarily stored by a microprocessor-controlled medical device, a variety of memory storage structures may be used. For example, a look up table (LUT) can be used to store the interval or ESI timing information and corresponding physiologic response and the like, and other computer readable storage media may be used. For example, as is known to those of skill in the art, serial access memory (SAM) buffers, random access memory (RAM) including dynamic and static variants thereof (DRAM, SRAM), and read only memory (ROM—also known as "firmware") and programmable and electrically erasable programmable variants thereof (PROM, EEPROM also known as "flash memory") and the like may be successfully used in practicing the present invention. In addition to storing data and information as just described other physiologic information may also be stored. For example, a resting condition heart rate, present or prior ESI, activity of daily living (ADL) condition heart rate, a sleeping condition heart rate, an upper tracking rate (UTR) condition heart rate, a lower tracking rate (LTR) condition heart rate, and the like may be stored in conjunction with the other stored data.

With regard to the electrode system illustrated in FIG. 1A, the IMD 10 is provided with a number of connection terminals for achieving electrical connection to the leads 6, 15, 16 and their respective electrodes. The connection terminal 311 provides electrical connection to the housing 11 for use as the indifferent electrode during unipolar stimulation or sensing. The connection terminals 320,310,318 provide electrical connection to coil electrodes 20,8,23 respectively. Each of these connection terminals 311, 320,310,318 are coupled to the high voltage output circuit 234 to facilitate the delivery of high energy shocking pulses to the heart using one or more of the coil electrodes 8,20,23 and optionally the housing 11. Connection terminals 311,320,310,318 are further connected to switch matrix 208 such that the housing 11 and respective coil electrodes 20,8,23 may be selected in desired configurations for various sensing and stimulation functions of IMD 10.

The connection terminals 317,321 provide electrical connection to the tip electrode 17 and the ring electrode 21 positioned in the right atrium. The connection terminals 317,321 are further coupled to an atrial sense amplifier 204 for sensing atrial signals such as P-waves. The connection terminals 326,324 provide electrical connection to the tip electrode 26 and the ring electrode 24 positioned in the right ventricle. The connection terminals 307,309 provide electrical connection to tip electrode 9 and ring electrode 7 positioned in the coronary sinus. The connection terminals 326,324 are further coupled to a right ventricular (RV) sense amplifier 200, and connection terminals 307,309 are further coupled to a left ventricular (LV) sense amplifier 201 for sensing right and left ventricular signals, respectively.

The atrial sense amplifier 204 and the RV and LV sense amplifiers 200,201 preferably take the form of automatic gain controlled amplifiers with adjustable sensing thresholds. The general operation of RV and LV sense amplifiers 200,201 and atrial sense amplifier 204 may correspond to that disclosed in U.S. Pat. No. 5,117,824, by Keimel, et al., incorporated herein by reference in its entirety. Generally, whenever a signal received by atrial sense amplifier 204 exceeds an atrial sensing threshold, a signal is generated on output signal line 206. P-waves are typically sensed based on a P-wave sensing threshold for use in detecting an atrial rate. Whenever a signal received by RV sense amplifier 200 or LV sense amplifier 201 that exceeds an RV or LV sensing threshold, respectively, a signal is generated on the corresponding output signal line 202 or 203. R-waves are typically sensed based on an R-wave sensing threshold for use in detecting a ventricular rate.

In one embodiment of the present invention, ventricular sense amplifiers 200,201 may include separate, dedicated sense amplifiers for sensing R-waves and T-waves, each using adjustable sensing thresholds, for the detection of myocardial activation and recovery times. Myocardial activation times may be measured when a signal exceeding an activation time sensing threshold is received by an R-wave sense amplifier included in RV or LV sense amplifiers 200 or 201, causing a corresponding activation time sense signal to be generated on signal line 202 or 203, respectively. Likewise, recovery times may be measured when a signal exceeding a recovery time sensing threshold is received by a T-wave sense amplifier included in RV or LV sense amplifiers 200 or 201, causing a corresponding recovery time sense signal to be generated on signal line 202 or 203, respectively.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion, defibrillation and ESS functions of the IMD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. In accordance with the present invention, digital signal analysis of a selected EGM (or subcutaneous ECG signals if available) is performed by microprocessor 224.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used.

The remainder of the circuitry illustrated in FIG. 2A is an exemplary embodiment of circuitry dedicated to providing ESS, cardiac pacing, cardioversion and defibrillation therapies. The timing and control circuitry 212 includes programmable digital counters which control the basic time intervals associated with ESS, various single, dual or multi-chamber pacing modes, or anti-tachycardia pacing therapies delivered in the atria or ventricles. Timing and control circuitry 212 also determines the amplitude of the cardiac stimulation pulses under the control of microprocessor 224.

During pacing, escape interval counters within timing and control circuitry 212 are reset upon sensing of RV R-waves, LV R-waves or atrial P-waves as indicated by signals on lines 202,203,206, respectively. In accordance with the selected mode of pacing, pacing pulses are generated by atrial output circuit 214, right ventricular output circuit 216, and left ventricular output circuit 215. The escape interval counters are reset upon generation of pacing pulses, and thereby control the basic timing of cardiac pacing functions, which may include bradycardia pacing, cardiac resynchronization therapy, and anti-tachycardia pacing.

The durations of the escape intervals are determined by microprocessor 224 via data/address bus 218. The value of the count present in the escape interval counters when reset by sensed R-waves or P-waves can be used to measure R—R intervals and P—P intervals for detecting the occurrence of a variety of arrhythmias.

In accordance with the present invention, timing and control 212 further controls the delivery of ESS at selected ESIs following either sensed intrinsic systoles or pacing evoked systoles. The ESIs used in controlling the delivery of ESS stimuli by IMD 10 are preferably automatically adjusted by IMD 10 based on physiologic and/or metabolic measurements during ESS therapy delivery. The output circuits 214,215,216 are coupled to the desired stimulation electrodes for delivering cardiac pacing therapies, including ESS therapy, via switch matrix 208.

The microprocessor 224 includes associated ROM in which stored programs controlling the operation of the microprocessor 224 reside. A portion of the memory 226 may be configured as a number of recirculating buffers capable of holding a series of measured intervals (e.g., R—R, P—P, etc.) for analysis by the microprocessor 224 for predicting or diagnosing an arrhythmia.

In response to the detection of tachycardia, anti-tachycardia pacing therapy can be delivered by loading a regimen from microcontroller 224 into the timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246,248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the timing and control circuitry 212 by an output circuit 234 via a control bus 238. The output circuit 234 determines the electrodes used for delivering the cardioversion or defibrillation pulse and the pulse wave shape.

In one embodiment, the implantable system may additionally include one or more physiological sensors for monitoring hemodynamic or myocardial contractile function or a metabolic status. The physiological sensor may reside within, about or on the heart, or endo- or extra-arterially for sensing a signal proportional to the hemodynamic function of the heart, myocardial contraction or heart wall motion, and/or a metabolic parameter. As such, IMD 10 is additionally equipped with sensor signal processing circuitry 331 coupled to a terminal 333 for receiving an analog sensor signal. A physiological sensor included in the implanted system may be, but is not limited to, a sensor of flow, pressure, heart sounds, wall motion, cardiac chamber volumes or metabolic parameters such as oxygen saturation or pH. Sensor signal data is transferred to microprocessor 224 via data/address bus 218 such that an index of cardiac hemodynamic or contractile performance or a metabolic status may be determined according to algorithms stored in RAM 226. Sensors and methods for determining a cardiac performance index as implemented in the previously-cited '098 patent to Bennett may also be used in conjunction with the present invention. As will be described in greater detail below, a mechanical or hemodynamic parameter of cardiac function or a metabolic parameter may be used in one embodiment of the present invention for controlling the ESI during ESS based on optimal mechanical enhancement of the post-extra-systolic beats. In another embodiment of the present invention, control of the ESI includes measurement of the mechanical restitution during extra systoles.

In general, the physiologic response to ESS therapy delivery may be measured from a sensor capable of generating a signal proportional to myocardial contraction or wall motion or hemodynamic performance. Such sensors include, but are not limited to, a pressure sensor, a flow sensor, one or more single- or multi-axis accelerometers, a heart sound sensor, an impedance sensor, and so forth. Alternatively, a sensor indicative of metabolic state, such as an oxygen saturation sensor or pH sensor, may used to monitor the patient status during ESS. An index of hemodynamic or myocardial contractile performance or metabolic state is determined from the sensed signal acquired during post-extra-systolic beats to determine the effectiveness of the extra systole in achieving mechanical ESS effects.

Figure 2B:
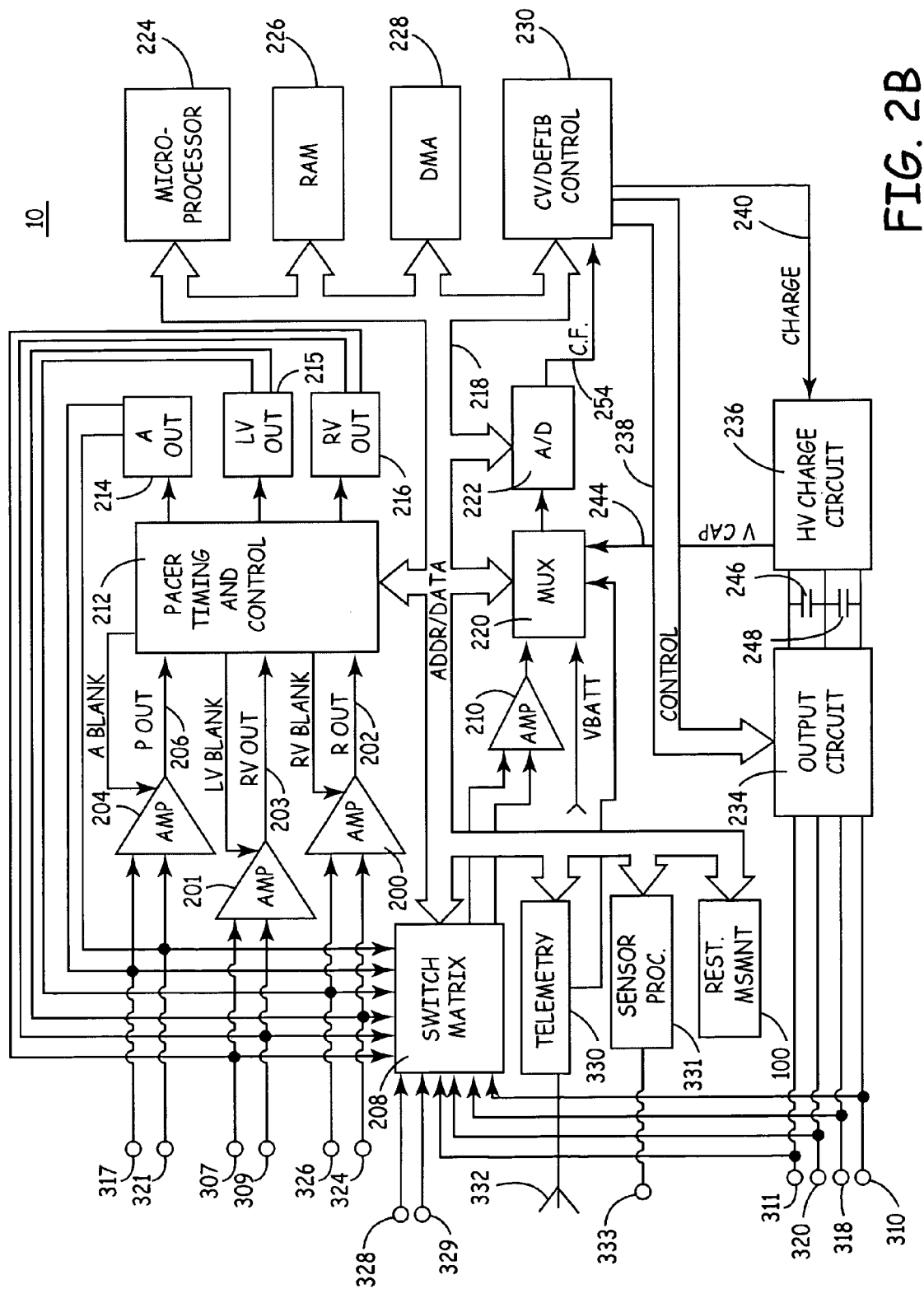
FIG. 2B is a functional schematic diagram of an alternative embodiment of the IMD, with regard to the electrode configuration of FIG. 1B, which includes dedicated circuitry for measuring electrical restitution.

FIG. 2B is a functional schematic diagram of an alternative embodiment of the IMD 10, which includes dedicated circuitry for monitoring electrical activity relating to ESS therapy delivery. The circuitry 100 is provided for receiving one or more EGM or subcutaneous ECG signals via switch matrix 208 and multiplexer 220 on address/data bus 218. In the embodiment of FIG. 2B and with regard to the electrode arrangement of FIG. 1B, connection terminals 328,329 are provided for connection to subcutaneous electrodes 30,32 incorporated in housing 11, for use in sensing ECG signals. EGM/ECG sensing vectors may be configured from any of the available electrodes via switch matrix 208. Measurement circuitry 100 processes the one or more selected EGM/ECG data signals for arrhythmia detection as well as setting pacing parameters. The related data signals and pacing parameters are conveyed to microprocessor 224 for use in controlling ESS. The data and parameters may be stored in device memory 226 for later uplinking to an external device such that it is available for review by a physician for cardiac monitoring purposes.

As indicated above, the measurement circuitry 100 may include dedicated circuitry for detecting myocardial recovery times following extra-systolic activation and measuring the intervening time interval. Recovery time detection circuitry may be provided as disclosed in co-pending non-provisional U.S. patent application Ser. No. 10/426,613 to Burnes et al. filed on 29 Apr. 2003 and incorporated herein by reference in its entirety. The above-noted patent application relates generally to a T-wave feature detector and recovery time estimator.

In one embodiment, the data and parameters are collected during ESS therapy delivery, when ESI adjustments are occurring (e.g., iterative ESI adjustments over a desired range and delivering ESS therapy for a period of time or number of cardiac cycles at each ESI). Extra-systolic stimuli may follow either or both sinus systoles or pacing-evoked systoles. Upon application of each ESS pacing therapy at a given ESI, a period of stabilization may be allowed prior to measuring the resulting intervals to allow the myocardial response to the change in ESI to reach a steady state.

Figure 3:
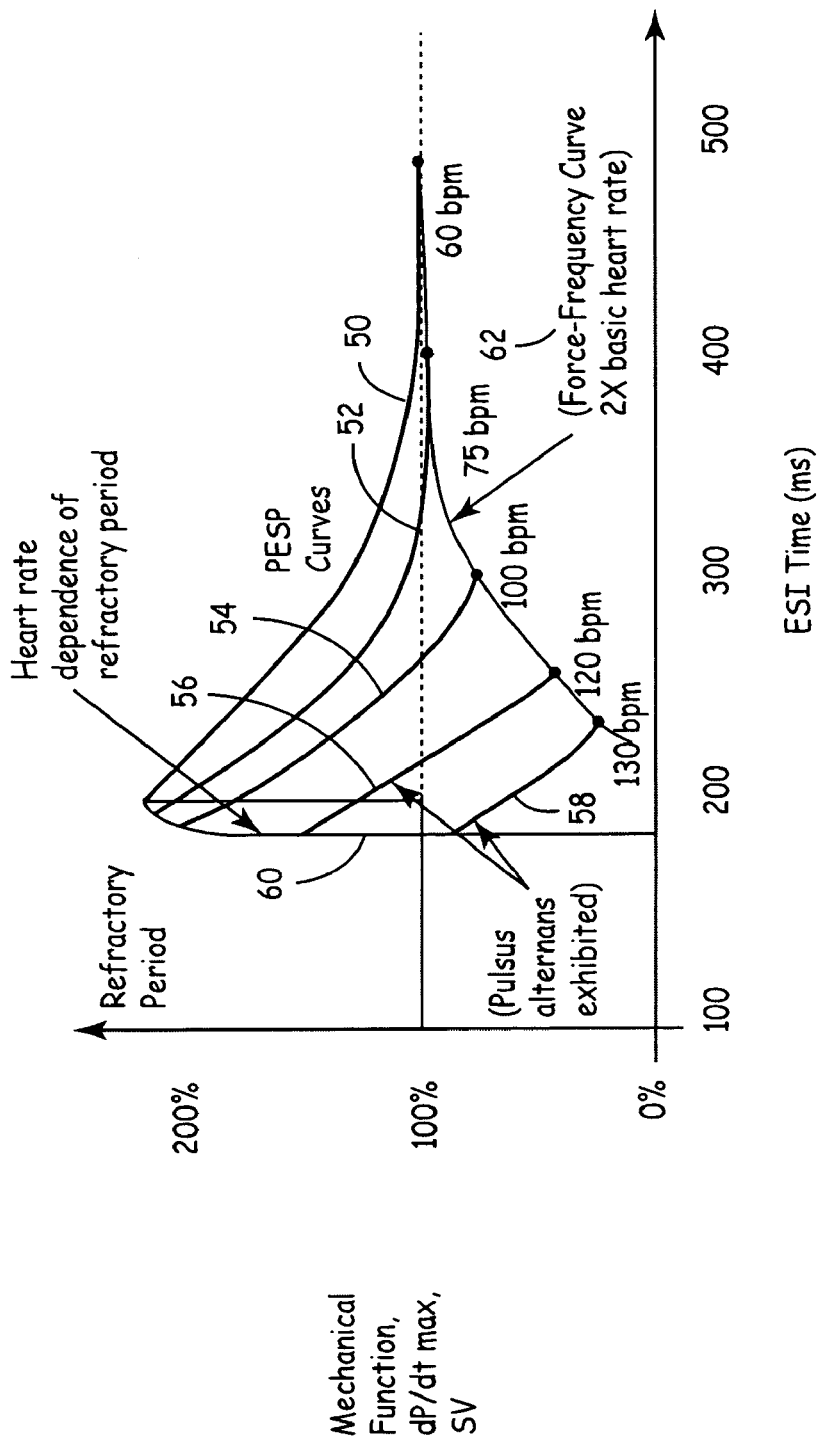
FIG. 3 is a graph depicting the interdependence of mechanical function, heart rate, and ESI.

Referring now to FIG. 3, which depicts the inter-relation among heart rate (HR), ESI, and hemodynamic effect during delivery of a PESP or an ESS therapy. In FIG. 3, the depicted curves 50,52,54,56,58 are parameterized by heart rate (HR). For example, curves 56,58 represent 120 and 130 beat per minute (bpm) HR, respectively, and both curves 56,58 illustrate impaired mechanical function for relatively high rate delivery of a PESP or ESS therapy. The refractory period (or region) 60 is also depicted in FIG. 3 and, as depicted, illustrates that the physiologic refractory period 60 has some dependence on HR. This phenomenon can be appreciated with reference to curved upper portion of the refractory period boundary 60 (as mechanical function increases approximately 200%).

In addition, as noted parenthetically in FIG. 3, symptoms of pulsus alternans were observed. Pulsus alternans is a beat-to-beat variation in a pressure tracing for an LV or RV of a patient. Pulsus alternans is believed to be a manifestation of decreased myocardial contractility. Such decreased myocardial contractility may be attributed to a reduced number of myocardial cells contracting on alternate beats. Another mechanism that may be involved is an alteration in diastolic volume leading to beat-to-beat variation in preload.

In any event, a safe an efficacious delivery of a ESS therapy avoids generating symptoms of pulsus alternans.

Continuing with reference to FIG. 3, each depicted curve 50–58 begins at the left hand side of the drawing (at an ESI just greater than the refractory period) and ends on the right hand side of FIG. 3 where the ESI is exactly one-half (½) of the mechanical ESS therapy HR (e.g., curve 50 illustrates a 60 bpm HR and an endpoint of the curve 50 occurs at a 500 ms ESI). This curve 62 represents an ESS therapy delivery boundary. The curve 62 resulted from the inventors empirically determining that for ESI values greater than this one-half value (the "50—50 line") extra-systole and post-extra-systole interchange and thus such ESI values should be avoided during therapy delivery. The locus of points on curve 62 thus provides a useful force frequency curve at twice the basic ESS therapy HR. The locus of points on the left hand side of these curves indicates the rate dependence of the refractory period 60 for the myocardium. The inventors discovered that efficacious ESS therapy delivery occurs within these bounding curves 60,62. As those of skill in the art can appreciate, at higher basic HRs the time available for diastole becomes on important limitation because effective ESS therapy adds an extra-systole. In effect, this is also a higher net HR (although as noted, pulsus alternans-like patterns may be observed at sufficiently high HRs). Importantly, inspection of FIG. 3 reveals that an ESI that is suitable at one HR (e.g., 250 ms at 60 bpm) can be counter productive at another HR (e.g., 120 bpm). Thus, delivery of an efficacious ESS therapy should take into account the somewhat nonlinear relationship between HR and ESI. For example, ESS therapy delivery should not occur at certain relatively high HRs such as, perhaps, over 75 bpm.

Figure 4:
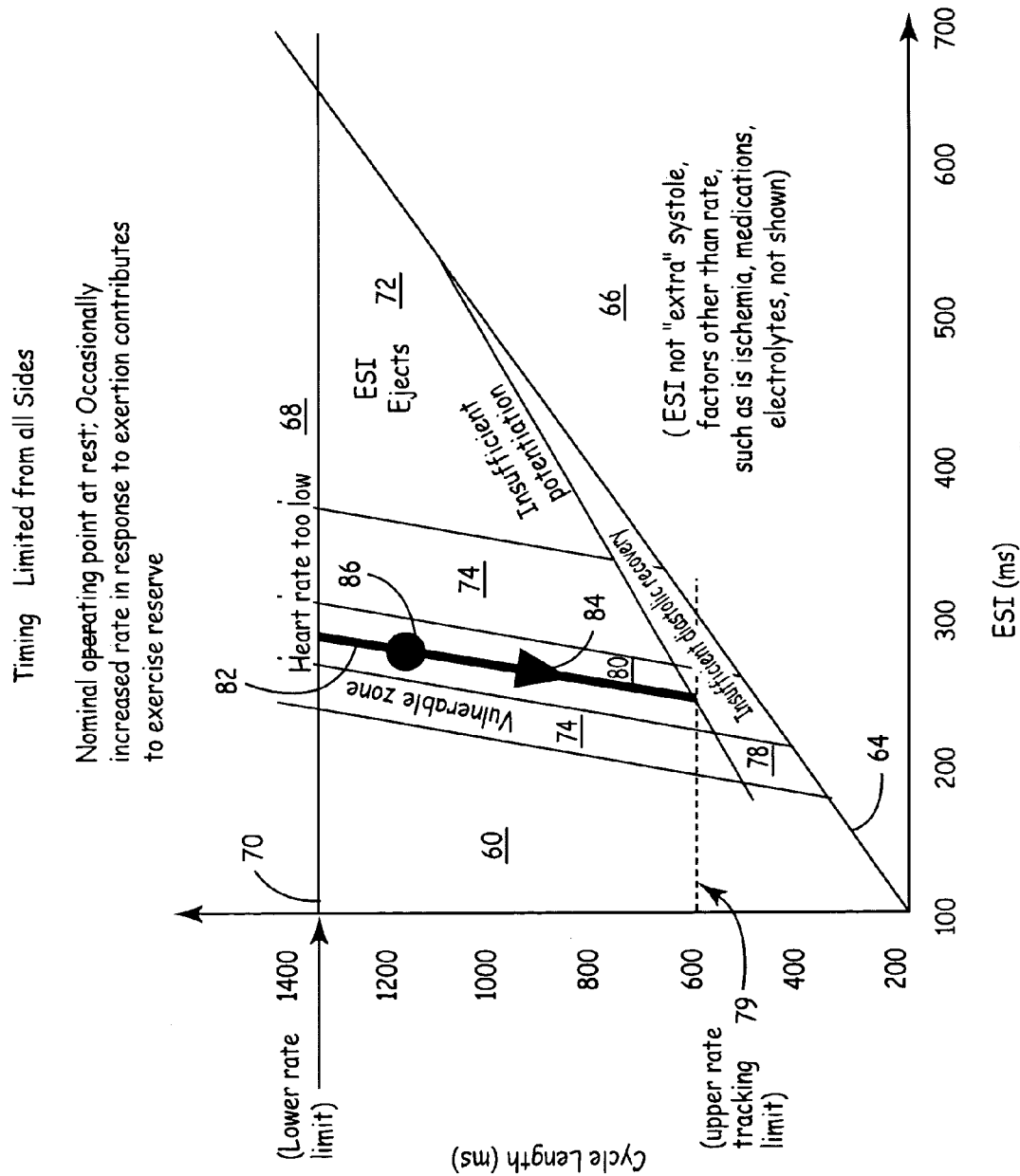
FIG. 4 is a graph depicting the relationship between cardiac cycle (in ms) and ESI (in ms) and the resulting physiologic response for combinations of ESI and cycle length.

Referring now to FIG. 4, the information depicted in FIG. 3 is shown as reinterpreted as constraints on ESI associated with HR (or cardiac cycle duration). In FIG. 4, the so-called "50—50 line" 64 appears wherein the ESI=½ cycle length on one side of the shaded triangle. The region 66 represents combinations of ESI and HR (expressed in millisecond cycle lengths) wherein no extra-systole can be invoked. Region 66 thus represents another ESS therapy delivery boundary.

The upper portion of FIG. 4 depicts a low HR boundary region 68 wherein for very low HRs such as those below the lower rate limit (denoted by horizontal line 70 involving very low stroke volume output, no longer rise (even with an invoked extra-systole) to improve cardiac output to an adequate level). The left-hand boundary region 60 reflects the dependence of refractory period on HR (idealized here as a straight line in lieu of the curved upper portion of line 60 in FIG. 3) over a range of HRs and ESIs. Thus, as illustrated in FIG. 4 the regions 60,66,68 define combinations of HR and ESI that ought to be avoided during ESS therapy delivery. In addition, the region 72 depicts combinations of ESI and HR wherein undesirable hemodynamic events can occur. For example, a volume of blood residing in a ventricular chamber following an initial systole ejects into the aorta during the extra-systole. This type of ejection may also manifest symptoms of pulsus alternans. Of course, the timing and rates of region 72 must be avoided during ESS therapy delivery. Likewise, region 74 depicts combinations of ESI and HR wherein an extra-systole response is evoked, but for which the evoked hemodynamic response is deemed insufficient. Thus, the timing and rates of region 74 should also be avoided during ESS therapy delivery. The region 76 labeled "Vulnerable zone" simply illustrates that the myocardium may become hyper-excitable for an interval of time following the refractory period (depicted as region 60). For this reason, the timing and rates of region 76 should also be avoided during ESS therapy delivery. Finally, the triangle-shaped region 78 illustrates combinations of ESI and cycle length (or HR) for which insufficient time is available for diastolic recovery of the myocardium. In addition, as indicated with reference to dashed horizontal line 79 (representing the upper tracking rate for a cardiac pacing engine) a large portion of region 78 is disposed below the upper tracking rate 79 and thus beyond detection limits of the cardiac pacing engine parameters depicted at line 79.

The remaining four-sided region 80 depicted in FIG. 4 thus illustrates suitable sets of pairings of HR (cycle length) and ESI for provision of a safe and efficacious ESS therapy. The HR and ESI pairings of region 80 are intended to provide a cardiac ESS therapy that: 1) remains out of (or away from) the refractory phase boundary region 60 and the arrhythmia vulnerable region 76, 2) maintains adequate minimal HR by avoiding region 68, 3) offers sufficient stroke volume augmentation to yield some clinical hemodynamic benefit(s) by avoiding region 74, and 4) leaves adequate time for diastolic recovery on a cycle-by-cycle basis by avoiding region 78.

Within the region 80 is a thin, black line segment 82. The line segment 82 illustrates that under physical exercise (or other tests of cardiac reserve), cycle length and ESI complement each other. That is, the combinations of ESI and HR of line segment 82 extending from the upper tracking rate limit (dashed line 79) which corresponds to a HR of approximately 100 bpm to the lower rate limit (line 70) which corresponds to a HR of approximately 50 bpm, provide optimal ESS therapy delivery. As also depicted in FIG. 4, is an arrow tip 84 connected to a circular feature 86. The line segment 82, arrow tip 84 and circular feature 86 as employed in FIG. 4 (and also in FIGS. 8–11 herein) are intended to convey relatively optimal ESS therapy delivery conditions for a limited range of HRs. In FIG. 4, the circular feature 86 depicts an optimal resting HR (of about 60 bpm) for ESS therapy delivery and the arrow tip 84 represents relatively optimal ESI as the HR increases (e.g., due to physical exertion). The length of the line segment connecting circular feature 86 and arrow tip 84 is intended to convey that while the full spectrum of relatively efficacious ESI and cycle length combinations depicted with line segment 82 may be employed during ESS therapy delivery, such therapy delivery should, as much as practicable, be limited to the combinations between circular feature 86 and arrow tip 84. As noted in the text appearing in region 66, the combinations of ESI and cycle length depicted in FIG. 4 are solely based on HR (cycle length) and do not account for other possibly confounding factors such as ischemia, presence of cardiac drugs, electrolyte imbalance and the like. Such possibly confounding factors are addressed hereinbelow and/or in the co-pending applications referred to and incorporated hereinabove.

Now turning to FIG. 5, four therapy delivery rates are depicted as line segments 50,52,54,56 representing 60 bpm, 75 bpm, 100 bpm and 120 bpm, respectively (consistent with the numbering used in FIG. 3). For each line segment 50–56, a relatively optimal "robust spot" 87 having an optimal choice of ESS therapy timing (i.e., ESI timing) depends on HR (and the definition of "optimal"). As described with respect to FIGS. 3 and 4, the limits of refractory period (region 60) and one half the mechanical cycle length (the "50—50 line" 64 in FIG. 4) essentially bound the range of physiologic and therapeutically useful ESI values. However, other factors contribute to defining an efficacious operating region such as that region 80 depicted in FIG. 4. With reference to FIG. 5, beginning at the edge of refractory period boundary 60, the zone of vulnerability (76 in FIG. 4) or enhanced risk of induced arrhythmias at relatively low stimulation amplitudes is represented by a solid black line segment (denoted 76). As depicted in FIG. 5, the zone of vulnerability 76 has been enlarged (i.e., lengthened) to incorporate an optional security margin (due primarily to the uncertainty of predicting or accurately measuring the possibly changing refractory period on a cycle-to-cycle basis), and thus, to a large extent, any attendant arrhythmia risk directly due to the ESS therapy delivery. At the other end of ESI, a solid line segment 78 represents the range of ESIs that will essentially result in a tachycardia and impair beneficial diastolic filling. The line segments 78 correspond to region 78 of FIG. 4. Unnoticeable at low HRs, the ESIs corresponding to segment 78 come to dominate possible ESIs at higher rates (e.g., compare line 56 for 120 bpm to line 50 for 60 bpm). Turning back to FIG. 3 it is apparent that such ESIs correspond to a zone wherein pulsus alternans was observed (as parenthetically noted in FIG. 3) as well as sub-baseline hemodynamics wherein mechanical function stands at less than 100%. Some of the benefits of properly administered ESS therapy presumably arise in enhanced cardiac mechanical performance and increased cardiac reserve(s). The gray "benefit" line segment (denoted by reference numeral 81) indicates ESI ranges where this benefit is prominent and extends from the edge of refractory period 60 to ESIs where there is little augmentation of stroke volume.

Designated by reference numeral 83, another gray "benefit" line segment appears. Line segment 83 illustrates a related but distinct beneficial mechanism that may be secondary to the HR lowering (e.g., halving) action of ESS therapy. The line segment 83 relates to the perception of the inventors that the relatively long cycle times and QT intervals are presumably due to withdrawal of catecholamines. The inventors posit that lower catecholamine exposure may result in beneficial regression of HF changes (also known as beneficial "reverse remodeling") and potentially reduced arrhythmias. This effect is more prominent at the higher levels of mechanical function.

Ideally, the ESI should be controlled to avoid the undesirable effects associated with line segments 76,78 and attempt to deliver an ESS therapy within the remaining portions of the cardiac cycle (denoted 81,83). The greatest benefit from ESS therapy delivery (assuming a fixed level of risk) appears to always reside at the lowest ESI outside the arrhythmia risk zone (line segment 76). As depicted in FIG. 5, the timing corresponding to this set of conditions is represented for each line 50–56 by circle 85. The circle 85 remains constant for each HR from 60 to 120 bpm. Alternatively, a dynamic maximally robust ESI timing (87) changes for each HR (corresponding to lines 50–56). While FIG. 5 provides another way of presenting the relationship between ESI and HR, the static ESI timing 85 (which is close to the end of the refractory period for all HRs) represents timing of the extra-systole to maximally augment stroke volume and the dynamic ESI timing 87 is progressively shorter at higher HRs. The dynamic ESI timing 87 thus balances the benefits stemming from reasonable stroke volume augmentation and the possible deleterious effects due to tachycardias and arrhythmia induction. Thus, it has been illustrated that the refractory period boundary 60 plays a key role in determining possible, secure, and beneficial ESS therapy timing. Particularly, when delivering ESS therapy at relatively high HRs, an ESS therapy pulse delivery may be intermittently placed at both ends of the possible range of the refractory boundary 60 (depicted by reference numeral 86 on line segment 56) to continuously track ESI and serve as a means of choosing an ESI that is securely beyond the zone of vulnerability 76 (and region 76 in FIG. 3) as disclosed in co-pending U.S. patent application Ser. No. 10/680528 filed on 7 Oct. 2003.

Now turning to FIG. 6 captioned, "VT Detection," the inventors have observed that, in general, robust detection of ventricular tachycardia (VT) events may be compromised during ESS therapy delivery because of the relatively high degree of periodic, post-therapy delivery blanking periods (a temporal blanking sequence is denoted by reference numeral 90) event sensing circuitry. As a result, a VT occurring at twice the mechanical HR can "hide" in the periodic blanking periods 91,93 imposed on the sensing circuitry for a ventricular pacing (Vpace blanking period 91) or an ESS therapy pulse (blanking period 93 for Vcp) as denoted by crossed-out "Vs" markers. Assuming the desirability of maximizing VT detection capabilities (and termination thereof) for a given HR, the inventors propose to deliver ESS therapy only within restricted, temporal "security zones" to avoid such a hidden VT. That is, to eliminate the opportunity for such a VT event to occur, for a selected HR of X bpm, ESS therapy delivery may be restricted to less than half the selected HR (<X/2 bpm). Although this approach alleviates the hidden VT problem it also places an upper rate limit for ESS therapy (of about 70 bpm). This situation is improved somewhat by utilizing a relatively short ESI and reducing the associated blanking period. For example, this combination permits the potentially hidden ventricular sense events ("Vs") to be sensed by the operative circuitry while an applicable security rule halts ESS therapy, thus allowing detection of such a VT. As illustrated in the upper and lower right panels of FIG. 6, at a fixed mechanical HR a VT condition can remain hidden over a range of ESIs equal to the blanking period 93 following an ESS therapy pulse (denoted "Vcp" in FIG. 6). The resulting interplay between hidden VT rate/interval and ESI is shown in FIGS. 8–11 below. The reason such hidden VT events exist appears to relate to present and prior art cardiac stimulation instrumentation, components and electrical circuitry. That is, the inability to further reduce ESI may perhaps be due to use of older, relatively high polarization medical electrical leads (and associated electrodes) and traditional sense amplifiers that have typically proven adequate for pre-existing, single-pacing-stimulus, cardiac stimulation devices. As is well known, ventricular fibrillation (VF) oftentimes comprises a frequent and aperiodic arrhythmia. As a result, given a shortest possible blanking interval of 150 ms (post Vpace and Vcp pulse delivery) VT detection can be compromised while VF detection is presumably little affected. This is due, in part, because typically the discrete VF intervals (occurring frequently and irregularly) are not readily masked by any periodic pacing stimulation (and related blanking) within a few cardiac cycles.

Referring to FIG. 7, a number of solutions have been proposed to improve VT detection, and the simplest methods involve either not continually delivering ESS therapy (pausing intermittently to allow VT detection) or limiting the ESS therapy delivery to an upper rate. Using short ESIs, particularly at higher rates (above 70 bpm) appears warranted from a VT detection standpoint as well as from a therapy delivery viewpoint (e.g., see FIG. 4). Reduced blanking and/or improved sensing can extend the upper rate limit range without withholding ESS therapy delivery (e.g., 20 ms shorter R—R intervals are possible with each 10 ms of reduced blanking). Also, auxiliary sensing vectors (e.g., RV-coil to canister electrode, can-based electrodes, surface electrodes and the like) can be employed to eliminate polarization problems often encountered with same-chamber sensing circuitry. A superior solution in continuous sensing would be to employ morphology discrimination means to discriminate a normal evoked response amplitude, time, and morphology from a VT. Another mode of ESS therapy delivery involves a therapy delivery platform configured to frequently (or periodically) withhold therapy delivery to, among other things, permit true VT rate and AV synchrony evaluations to proceed. Withholding ESS therapy at some ratio (e.g., 1:4, 1:6, 2:7, etc.) could also be employed so that arrhythmia detection may occur on a periodic basis. In any event, if a VT episode having a reasonably constant rate aligns near an ESI boundary the VT rate can reasonably be expected to show some level of variation so that the VT episode would eventually be detected, but at the price of delayed detection. Thus, the outer boundaries for VT rates can be viewed as estimated boundaries with the interior portions less likely to exceed the outer boundaries. In FIG. 7 (and FIG. 8), "VTDI" stands for VT detection interval which is typically expressed in milliseconds (ms). A typical VTDI of 400 ms represents a 150 bpm HR.

Figure 8:
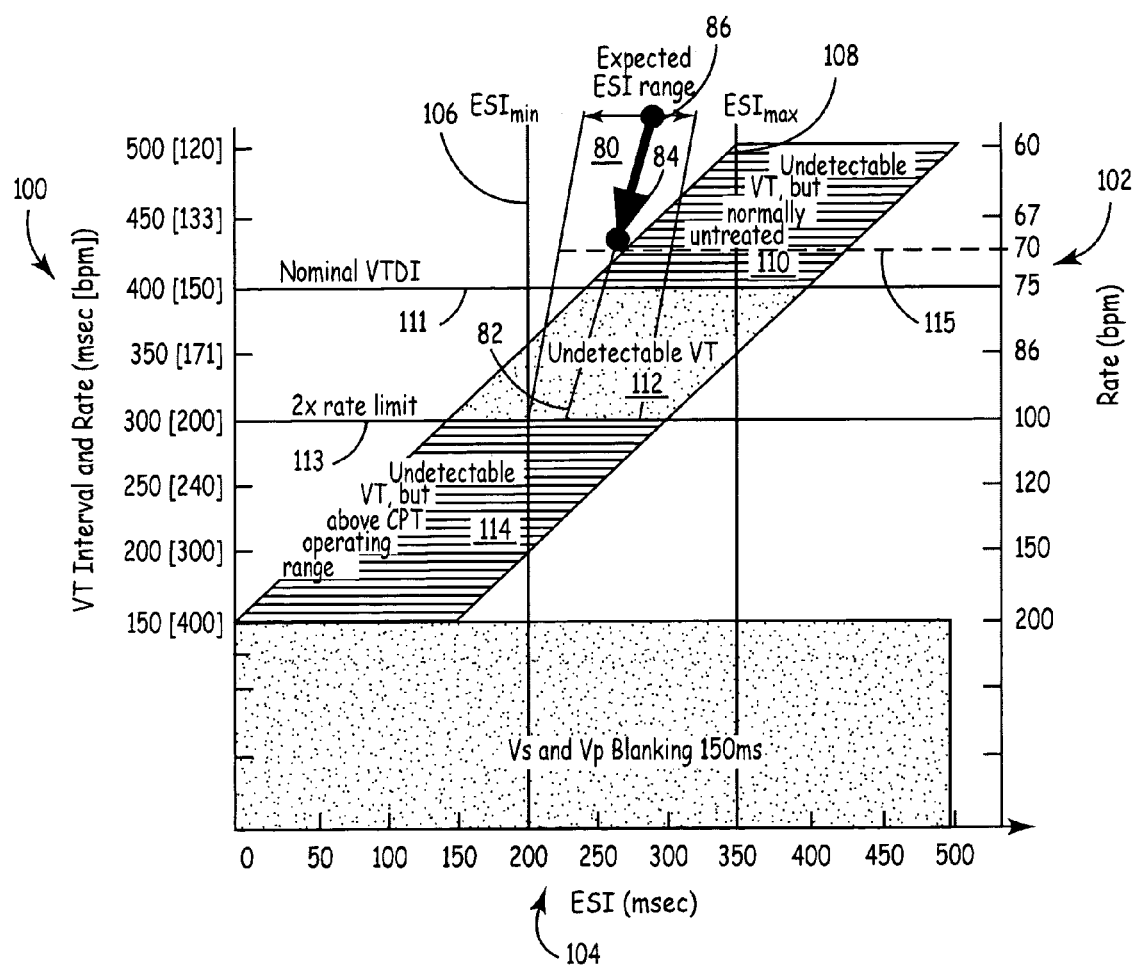
FIG. 8 is a graph wherein VT detection intervals and VT rates are correlated to an ESS therapy delivery rate for a range of ESIs.

FIG. 8 is a graph wherein VT detection intervals and VT rates (denoted with reference numeral 100) are correlated to an ESS therapy delivery rate expressed in bpm (denoted by reference numeral 102) for a range of ESIs from 0 to 500 ms (denoted with reference numeral 104). A pair of blanking intervals, one for each pair of ventricular depolarizations during ESS therapy delivery (Vs and Vcp) of 150 ms in duration were used in formulating FIG. 8. As a result of the 150 ms blanking periods, a 150 ms-wide region of potentially undetected VT episodes is illustrated (regions 110,112, 114) in FIG. 8. The regions 110,112,114 thus practically constrain ESS therapy delivery, as described hereinbelow. As depicted, the range of actual ESIs begins with a minimum ESI of 200 ms (vertical line 106) and ends with a maximum ESI of 350 ms (vertical line 108). FIG. 8 is intended to better Illustrate hidden VT and ESI interactions described herein. Beginning with an arbitrary ESS therapy delivery rate range (e.g., about 60–100 bpm) and a VT detection interval lower limit of 150 bpm (400 ms), several therapy delivery boundary conditions and arrhythmia detection issues arise. For example, a region 110 corresponds to the characteristics of undetectable (and typically untreated) VT having a rate of between 120 bpm and 150 bpm. Said VT are deemed undetectable because they occur with the same frequency as a normal activity (including sinus tachycardia) and, as depicted, have a lower rate (and higher interval) than the nominal VTDI. The nominal VTDI has an interval threshold of 400 ms and a threshold rate of 150 bpm (as indicated by horizontal line 111). Region 112 depicts a second family of undetectable VT having a rate of between 150 bpm and 200 bpm. In FIG. 8, a reasonable set of ESS therapy delivery conditions (similar to the set described with reference to FIG. 4) defines a parallelogram-shaped region 80. The region 80 is bounded by the 2× rate limit (200 bpm) for a 100 bpm maximum therapy delivery rate and intersected by both of the undetectable VT regions 110, 112. The region 80 thus defines limited sets of relatively poor-performing ESI and VT interval combinations. The region 80 is furthermore depicted as practically bounded to a set of relatively secure combinations of ESI and HR as depicted by the upper portion of line segment 82. More particularly, the circular feature 86 represents a nominal, low HR combination of ESI and HR and, arrow 84 represents the ESI for a (maximum therapy delivery) HR of about 70. This HR approximately coincides with the intersection of line segment 82 and the undetectable VT region 110 (and is represented by dashed line 115). In the example depicted in FIG. 8 (and absent morphology-based VT detection), the combination of ESI, VT detection and HR results in a practical upper limit for ESS therapy delivery of about 70 bpm. If a higher continuous ESS therapy delivery rate is desired such delivery will occur with an attendant risk of undetected VT. As noted with respect to FIG. 7, intermittent delivery of an ESS therapy at a rate above 70 bpm could occur (e.g., while dropping ESS therapy beats or implementing other measures in order to enhance VT detection). This result provides a sharp contrast with the results depicted in FIGS. 9–11 below.

Figure 9:
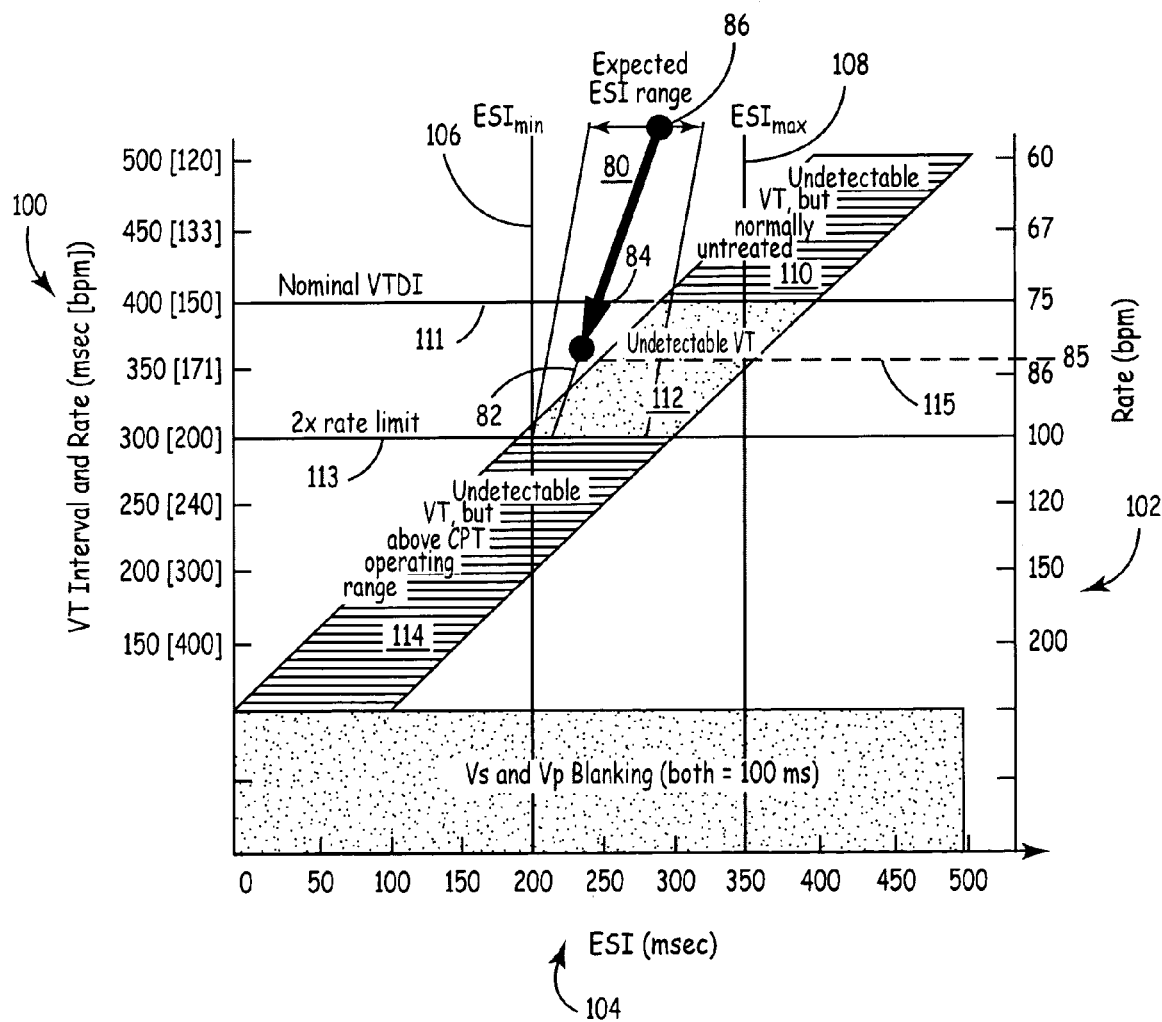
FIG. 9 is a graph wherein VT detection intervals and VT rates are correlated to an ESS therapy delivery rate for a range of ESIs.

Referring now to FIG. 9, which shares the basic format of FIG. 8, an illustration of hidden VT and ESI interactions with relatively less blanking than FIG. 8 above. As explained below, shortened blanking intervals (i.e., 100 ms versus 150 ms in FIG. 8), results in a relatively extended ESS therapy delivery operating rate range. As depicted in FIG. 9, the therapy delivery operating range extends to about 85 bpm. These additional 15 bpm (over the therapy delivery regime of FIG. 8) provide an effective exertional cardiac reserve, especially given the associated augmented mechanical performance. As depicted, the range of actual ESIs begins with a minimum ESI of 200 ms (vertical line 106) and ends with a maximum ESI of 350 ms (vertical line 108). FIG. 9 again illustrates hidden VT and ESI interactions during ESS therapy delivery. Beginning with an arbitrary ESS therapy delivery rate range (e.g., about 60–100 bpm) and a VT detection interval (VTDI) lower limit of 150 bpm (400 ms), several therapy delivery boundary conditions and arrhythmia detection issues arise. For example, the region 110 corresponds to the characteristics of undetectable (and typically untreated) VT having a rate of between 120 bpm and 150 bpm. Said VT are deemed undetectable because they occur with the same frequency as a normal activity (including sinus tachycardia) and, as depicted, have a lower rate (and higher interval) than the nominal VTDI. The nominal VTDI has an interval threshold of 400 ms and a threshold rate of 150 bpm (as indicated by horizontal line 111). Region 112 depicts a second family of undetectable VT having a rate of between 150 bpm and 200 bpm. In FIG. 9, a reasonable set of ESS therapy delivery conditions (similar to the set described with reference to FIG. 4) defines a parallelogram-shaped region 80. The region 80 is bounded by the 2× rate limit (i.e., 200 bpm) as shown by horizontal line 113 for a 100 bpm maximum therapy delivery rate. The region 80 overlaps primarily with the undetectable VT region 112. The region 80 thus defines limited sets of ESI and VT interval combinations for secure ESS therapy delivery, albeit less limited than the combinations depicted in FIG. 8. The region 80 is furthermore depicted as practically bounded to a set of relatively secure combinations of ESI and HR as depicted by the major upper portion of line segment 82. More particularly, the circular feature 86 represents a nominal, relatively low (60 bpm) HR at an ESI of about 300 ms. Arrow 84 represents a maximum therapy delivery HR of about 85 bpm at an ESI of about 250 ms. This HR approximately coincides with the intersection of line segment 82 and the border of undetectable VT region 112 (and is represented by dashed line 115). In the example depicted in FIG. 9 (and absent morphology-based VT detection), the combination of ESI, VT detection and HR results in a practical upper limit for ESS therapy delivery of about 85 bpm. If a higher continuous ESS therapy delivery rate is desired such delivery will occur with an attendant risk of undetected VT. As noted with respect to FIG. 7, intermittent delivery of an ESS therapy at a rate above 85 bpm could occur (e.g., while dropping ESS therapy beats or implementing other measures in order to enhance VT detection).

Figure 10:
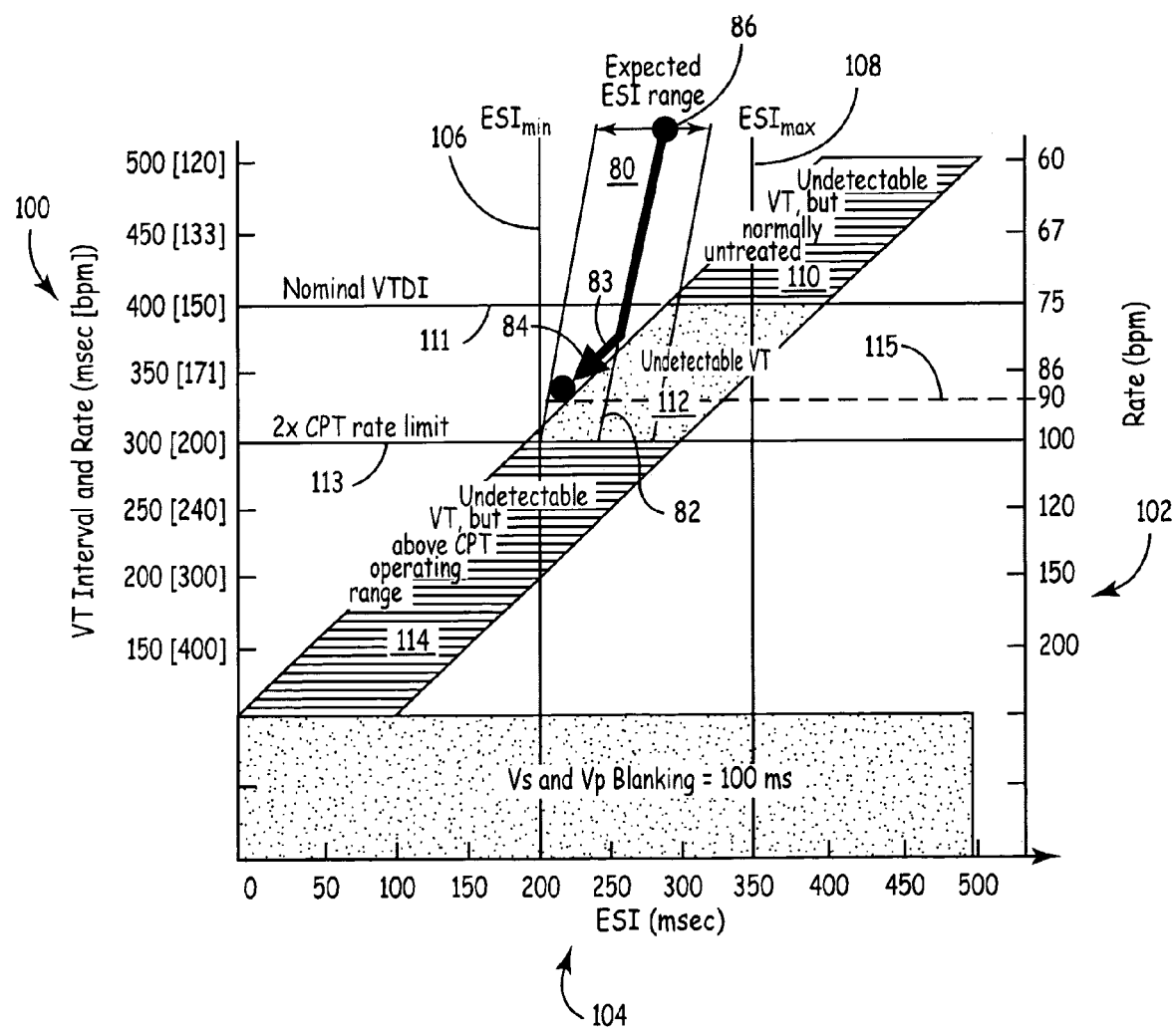
FIG. 10 is a graph wherein VT detection intervals and VT rates are correlated to an ESS therapy delivery rate for a range of ESIs.

With reference to FIG. 10, a further increase of a secure ESS therapy operating range is illustrated (i.e., from 40 bpm to 90 bpm) without resorting to dropped ESS therapy delivery during a given cardiac cycle as a result of implementing a further rule on the ESI relationship to HR that keeps ESI shorter than can hide a VT episode. In FIG. 10, the post-ventricular event blanking is set at 100 ms (the same as FIG. 9). As depicted in FIG. 10, the therapy delivery operating range extends to about 90 bpm. These additional 5 bpm (over the therapy delivery regime of FIG. 9) provide an added exertional cardiac reserve, especially given the associated augmented mechanical performance. As depicted, the range of actual ESIs begins with a minimum ESI of 200 ms (vertical line 106) and ends with a maximum ESI of 350 ms (vertical line 108). Like FIGS. 8 and 9, FIG. 10 again illustrates hidden VT and ESI interactions during ESS therapy delivery. Beginning with an arbitrary ESS therapy delivery rate range (e.g., about 60–100 bpm) and a VT detection interval (VTDI) lower limit of 150 bpm (400 ms), several therapy delivery boundary conditions and arrhythmia detection issues arise. For example, the region 110 corresponds to the characteristics of undetectable (and typically untreated) VT having a rate of between 120 bpm and 150 bpm. Said VT are deemed undetectable because they occur with the same frequency as a normal activity (including sinus tachycardia) and, as depicted, have a lower rate (and higher interval) than the nominal VTDI. The nominal VTDI has an interval threshold of 400 ms and a threshold rate of 150 bpm (as indicated by horizontal line 111). Region 112 depicts a second family of undetectable VT having a rate of between 150 bpm and 200 bpm. In FIG. 10, a reasonable set of ESS therapy delivery conditions (similar to the set described with reference to FIG. 4) defines a parallelogram-shaped therapy delivery region 80. The region 80 is bounded by the 2× rate limit (i.e., 200 bpm) as shown by horizontal line 113 for a 100 bpm maximum ESS therapy delivery rate. As with FIG. 9, the region 80 overlaps primarily with the undetectable VT region 112. The region 80 thus defines limited sets of ESI and VT interval combinations for secure ESS therapy delivery, albeit less limited than the combinations depicted in FIGS. 8 and 9. The region 80 is practically bounded to a set of relatively secure combinations of ESI and HR as depicted by the major upper portion of line segment 82. More particularly, the circular feature 86 represents a nominal, relatively low (approximately 60 bpm) HR at an ESI of about 300 ms. Arrow 84 represents a maximum therapy delivery HR of about 90 bpm at an ESI of about 225 ms. This HR approximately coincides with a divergent therapy delivery line segment (or vector) 83 which begins where the original therapy delivery line segment 82 and the undetectable VT region 112 intersect. The divergent therapy delivery vector 83 stems from the original therapy line segment 82 so as to safely avoid the undetectable VT region 112 (and is represented by dashed line 115). In the example depicted in FIG. 10 the combination of ESI, VT detection regions and HR results in a practical upper limit for ESS therapy delivery of about 90 bpm. The divergent therapy delivery vector 83 is readily calculated since the sensing and blanking characteristics are known. Thus, computational circuitry within the ESS therapy delivery device can determine if the HR is increasing to the point such that a hidden VT (undetectable VT) can occur, and adjust the timing accordingly. The combinations of ESI and HR of the vector 83 thus represents secure, higher rate ESI-HR therapy delivery combinations. These combinations are secure so long as the precautions regarding therapy delivery in the vulnerable zone (regarding pulse amplitude and timing restrictions) are observed. Such precautions are described with reference to FIG. 13 (below). This new therapy delivery vector 83 further extends the upper rate for ESS therapy delivery by moving away from the undetectable VT zone 112 and toward a relatively more secure therapy delivery location within region 80.

In support of a transitional rule for the type of higher rate ESS therapy delivery depicted in FIG. 10 the inventors offer the following rationale. Assume that the basic ESS therapy delivery cycle length to ESI (CL to ESI) relationship can be represented mathematically as $ESI_{indicated} = f(CL)$ which may, for example, consist of an offset power relation (like Bazett's formula+constant) or a simple straight line function: $f(CL) = a \times CL + b$. Incidentally, Bazett's formula corrects or normalizes the measured QT interval for a heart rate of 60 bpm. Thus, the QT is measured at the given heart rate, and a corrected QT (QTc) estimates what the QT interval would be if the heart rate were 60. By comparing the indicated ESI with the borders of undetectable VT regions (110, 112, 114) defined by the ESS therapy cycle length and the blanking interval (BI) as follows: If $f(CL) > CL/2 - BI$, then ESI is instead set to $CL/2 - BI$. The function parameters may be chosen from empiric testing of the refractory period at paced rates during implant with an offset to reduce the chance of inducing an arrhythmia.

Figure 11:
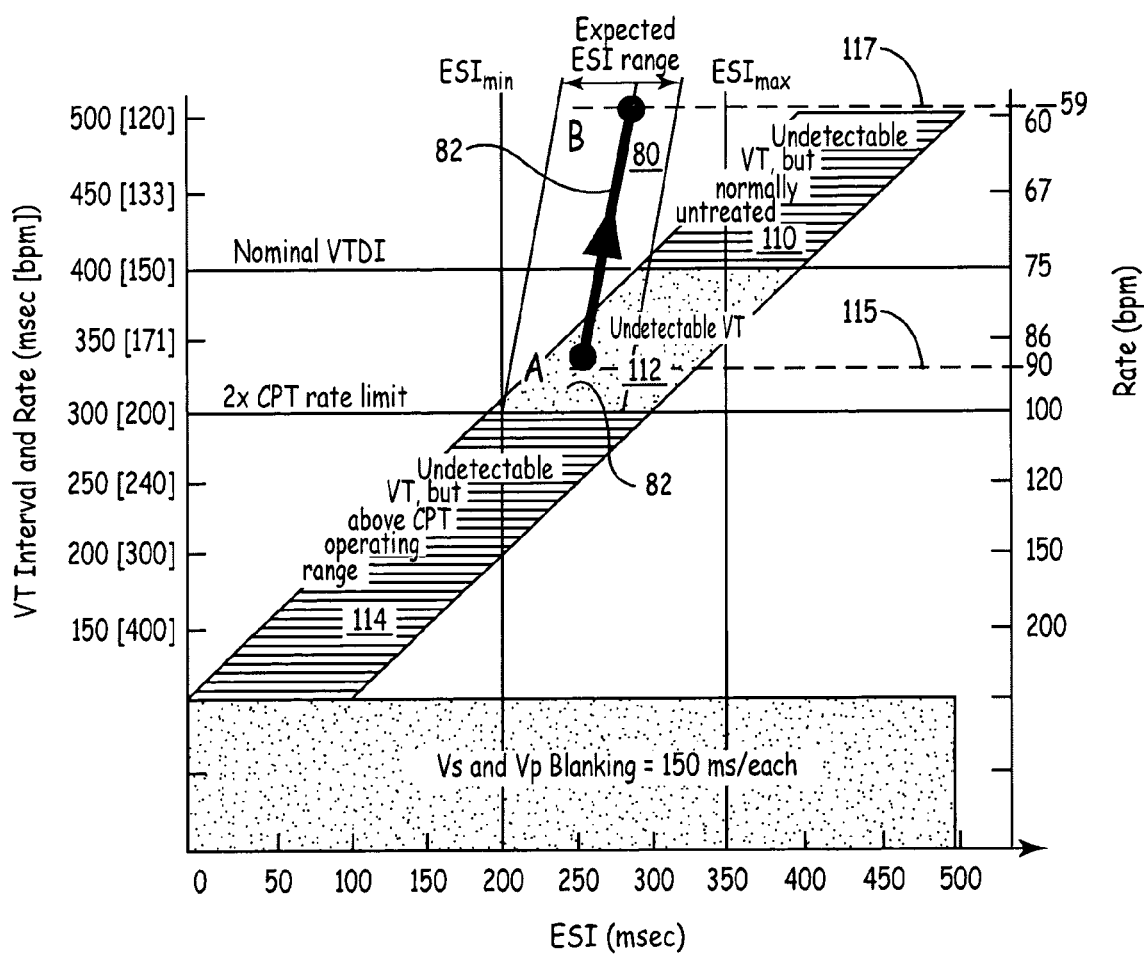
FIG. 11 is a graph wherein VT detection intervals and VT rates are correlated to an ESS therapy delivery rate for a range of ESIs.

Referring now to FIG. 11, a transient override of the HR limits previously discussed is depicted. The override permits delivery of an ESS therapy with mediated HR reductions. The inventors have observed that the onset of effective ESS therapy frequently is accompanied by a prompt reduction of HR. Since this occurs over just a few cardiac cycles, there is little point to requiring a dropped ESS therapy cycle or departing from the indicated ESI (as discussed above) in response to HR reduction during ESS therapy delivery. If the HR falls to a point where hidden VTs are no longer possible, the indicated ESI is followed. This is a form of history-dependent or hysteresis behavior that depends on the HR starting at a relatively high level and promptly falling to a reduced level during delivery of ESS therapy within the relatively secure therapy delivery region 80. As depicted in FIG. 11, a patient having a HR of approximately 90 bpm during ESS therapy delivery (at feature labeled "A") with an ESI of approximately 250 ms may be exposed to a hidden VT (i.e., the ESI-HR combination lies within region 112). The inventors propose that in this situation, rather than disabling ESS therapy delivery to enhance VT detection or employing a divergent vector 83 as described in reference to FIG. 10, the ESI is extended to approximately 300 ms to reduce the HR to as low as about 60 bpm (at the feature labeled "B"). In this situation the ESI may be initially rapidly extended along the line segment 82 until the ESI-HR therapy delivery combination no longer lies within region 112. Then, the ESI may be gradually extended to a higher value. However, the magnitude and rate of the ESI extension is a matter of clinical preference. Thus, a gradual rise in HR from 90 bpm at point "B" (also indicated by dashed line 115) to about 59 bpm at point "A" (indicated by dashed line 117) occurs during continuous ESS therapy delivery. The inventors promote this aspect of the present invention as a transient override because of the latent potential of an undetectable VT episode during chronic ESS therapy delivery within any of the regions 110, 112, 114. That is, delivering ESS therapy having ESI-HR combinations that fall within said regions—without dropping ESS therapy or modifying ESI—is not considered an adequately secure chronic ESS therapy delivery regimen.

Turning now to FIG. 12, a graphical depiction of the so-called vulnerable zone (as earlier described in relation to FIG. 4) in terms of stimulation amplitude (expressed in volts) on the ordinate axis and ESI (expressed in milliseconds) on the abscissa axis. In FIG. 12 the vulnerable zone appears as a sub-dividable region distinguished from typical ESS therapy delivery parameters of approximately 200 ms to 300 ms ESI interval and a stimulation amplitude of about 0.4 V to about 4 V (represented by box 80). For the purposes of the illustration of FIG. 12, the vulnerable zone essentially comprises all combinations of ESI timing and stimulation amplitude that do no fall within either the refractory period 60 or the ESS therapy delivery regime 80. Thus, the vulnerable zone consists of open-ended region 92 and bounded regions 94,96,98. The bounded regions 94,96,98 are separated by both higher amplitude and timing within about 20 ms of the edge of the refractory period 60. FIG. 12 represents the results of acute laboratory testing, which unfortunately only provide estimated boundary contours of arrhythmia incidence and do not include possibly confounding factors affecting arrhythmia incidence. Thus, the bounded regions 94,96,98 correspond to different probabilities that an arrhythmia episode will occur for a given number of ESS therapy delivery cycles. For example, region 98 represents combinations of ESI and stimulus amplitude that will produce an arrhythmia for one cycle of ESS therapy out of every ten cycles of therapy delivery. The region 98 ($10^{-1}$) is surrounded by region 96 ($10^{-3}$) wherein one arrhythmia episode can be expected to occur out of 100 cycles of ESS therapy delivery. Region 94 surrounds region 96 and illustrates combinations of ESI and stimulus amplitude wherein one episode of arrhythmia can be expected to occur for every one million cycles of ESS therapy delivery. The unbounded region 92 illustrates that all other possible combinations of ESI and stimulus amplitude result in one arrhythmia for every billion cycles of ESS therapy delivery. The inventors conclude that the intrinsic likelihood of an arrhythmia in a given patient population without ESS therapy or with ESS therapy delivery (provided during the refractory period or at a sub-threshold level of energy delivery) is on the order of $10^{-9}$. Assume, for example, the likelihood of an arrhythmia rises to $10^{-7}$ within 20 ms of the boundary of the refractory period 60 having an ESS therapy pulse amplitude of 4 V, and a probe pulse to identify the refractory period 60 is given once every 500 cardiac cycles. If the ESI set without benefit of a probe pulse wanders into the $10^{-7}$ region about 1% of the time, there is now a greater risk of operation without probe pulses to track the refractory period than with them. This is the argument for implementing an automated refractory period test into a device and possibly using it more often than simply during post-implant testing. In any event, even if only a research tool, these probability contours (of regions 94,96,98) as empirically and objectively determined, constitute the most rigorous evidence of the limited risk of arrhythmia induction during ESS therapy delivery.

Of course, the therapy delivery rules and related methods according to the present invention may be embodied in executable instructions stored on a computer readable medium. The instructions stored on the computer readable medium are executed under processor control. All types of processors and computer readable media are expressly covered hereby. Said methods may be practiced by a single processor or a network of processors and/or certain steps of said methods may be practiced remote from processors that handle certain other of the steps of the foregoing methods.

The methods may be programmed wirelessly to modify, enhance, initiate or cease operations and data and parameters related to delivery of an ESS therapy may be stored for later retrieval and study. The number of cycles of any discrete combination of ESI and HR may be stored, or manipulated to provide average, mean, maximum, minimum values and the like. Such values may be stored in relation to other parameters (e.g., physiologic histograms, sensor measurements, etc.), so that more data regarding the ESS therapy delivery may be investigated.

In one embodiment, ESS therapy delivery is controlled based on both the heart rate and the ESI for a given extra-systolic stimulus. By controlling the ESI and the delivered extra-systolic stimulus (e.g., pulse width or duration, magnitude, polarity, etc.) over a relatively secure region of operation that avoids undue risk of arrhythmia episodes, ESS therapy delivery provides hemodynamic and mechanical enhancement for a wide variety of patients.

As can be appreciated with reference to the drawings and the written description, the interaction(s) between HR, ESI and hemodynamics illustrate that the benefits of ESS therapy delivery can be safely delivered within certain boundaries. In this regard, the so-called "50—50 line" wherein the HR is exactly twice (2×) an operating ESI deserves additional attention. The reason is that this condition provides a situation wherein a rate-doubled tachycardia can occur (that is not accompanied by any augmentation of stroke volume). For certain ESI and HR combinations such a tachycardia also can reside within an undetectable VT zone (e.g., zone 110, 112, 114 of FIGS. 8–11). For these reasons another aspect of the ESS therapy delivery guidance according to the present invention is the prohibition of any such "50—50" ESI-HR combinations during ESS therapy delivery.

In addition, after considerable study of the interaction(s) between HR, ESI and hemodynamics the inventors observed (and hereby emphasize) the need to control ESIs from being too long for a given cardiac cycle length and to match ESI (or "map" the ESI) to HR. Also, the inventors have observed that a step reduction in the applied ESI routinely leads to a transient period of increased HR and lower maximum rate of change of developed pressure ($dP/dt_{max}$). The resulting rise of HR, albeit transient, acts together with the relatively long ESI to accentuate this non-optimal therapy delivery paradigm. As a result, HR rises even further, while ESI is slowly being reduced. If the ESI reductions are too slow, cardiac output remains low and unstable, oscillating up and down. If the ESI is reduced to 240 ms (an ESI just 40 or so millisecond beyond an observed refractory period and very tolerant of high HRs) the HR typically further increases. As a result of these observations the inventors suggest that ESI adjustments occur fairly rapidly so that any possibly disadvantageous transient therapy response is limited. Such transient therapy responses furthermore encourage constant delivery of the relatively secure combinations of ESI and HR described herein in lieu of halting therapy (e.g., to improve VT detection). The inventors have also observed therapy response for healthy and heart failure-induced subjects. Importantly, they found that while the post-extrasystolic stroke volume augments for a healthy patient might continue for six or so cardiac cycles beyond cessation of an ESS therapy the potentially beneficial effects of ESS therapy delivered to a patient suffering from heart failure ends almost immediately. Thus, the inventors posit that chronic, uninterrupted ESS therapy delivery to a heart failure patient forms part of the therapy delivery guidance according to the present invention.

Thus, an implantable system and associated methods for the secure and efficacious delivery of an ESS therapy have been described and depicted. The present invention allows the hemodynamic benefits of post-extra-systolic potentiation to be gained in an electrical stimulation therapy for treating cardiac mechanical insufficiency while preventing an increased arrhythmia risk. While the present invention has been described according to specific embodiments presented herein, these embodiments are intended to be exemplary, not limiting, with regard to the following claims.

The invention claimed is:

1. A method for one of delivering and withholding delivery of an extra-systolic stimulation cardiac pacing therapy, comprising:

sensing electrical activity of a heart to provide a heart rate signal for said heart;

correlating the heart rate signal and an extra-systolic interval for an extra-systolic stimulation therapy to a data set having at least a plurality of heart rates and a plurality of extra-systolic intervals; and based on the correlation either delivering or inhibiting delivery of the extra-systolic stimulation therapy, wherein the data set includes empiric heart rate-based guidance for refractory period changes of a chamber of the heart for a plurality of heart rates, and evoked response information, and wherein said information is derived from measurements of an evoked response from the extra-systolic stimulation therapy, said information establishing, for at least one cardiac cycle, a refractory period of the chamber of the heart.

2. A method according to claim 1, wherein said information comprises at least one of: an evoked R-wave response, an evoked R-wave timing parameter, an evoked R-wave morphology characteristic, an evoked P-wave response, an evoked P-wave timing parameter, an evoked P-wave morphology characteristic, an evoked T-wave response, an evoked T-wave timing parameter, an evoked T-wave morphology characteristic, a ventricular pressure signal, an atrial pressure signal, a change of magnitude of a maximum derivative of the ventricular pressure signal, a change of magnitude of a maximum derivative of the atrial pressure signal.

3. A method according to claim 1, wherein at least some of said plurality of correlated heart rates and extra-systolic intervals incorporate reduced extra-systolic intervals for a set of relatively higher heart rates.

4. A method according to claim 1, wherein at least some of said plurality of correlated heart rates and extra-systolic intervals incorporate increased extra-systolic intervals for a set of relatively lower heart rates.

5. A method according to claim 3, wherein said correlated heart rates and extra-systolic intervals incorporate a security-timing margin for a tachycardia induction portion of the data set.

6. A method according to claim 1, wherein the data set; incorporates information regarding a predicted degree or a measured degree of a stroke volume augmentation resulting from at least some discrete combinations of the data set.

7. A method according to claim 1, wherein the data set incorporates information regarding enhanced arrhythmia detection.

8. A method according to claim 7, wherein the data set includes potential for a masked tachycardia rhythm, and further comprising:

periodically withholding delivery of the extra-systolic stimulation therapy or decreasing the extra-systolic interval.

9. A method according to claim 7, further comprising:
intermittently withholding delivery of the extra-systolic stimulation therapy for at least one cardiac cycle for every N cardiac cycles to expose a masked tachycardia rhythms, wherein N comprises a non-zero integer.

10. A method according to claim 7, wherein the information regarding enhanced arrhythmia detection includes a reduced electrogram blanking period following delivery of a cardiac pacing stimulation pulse or an extra-systolic stimulation pulse.

11. A method according to claim 10, wherein the reduced electrogram blanking period includes a cross-chamber blanking period and a same-chamber blanking period.

12. A method according to claim 10, wherein the reduced blanking extends at least one arrhythmia sensing interval for at least a portion of relatively higher heart rates mapped to a table.

13. A method according to claim 1, wherein the data sets incorporates information regarding a diastolic compromise condition.

14. A method according to claim 1, wherein for a plurality of relatively low heart rates: delivering the extra-systolic stimulation therapy for every cardiac cycle; and for a plurality of relatively high heart rates:
withholding delivery of the extra-systolic stimulation therapy.

15. A method according to claim 14, further comprising:
applying an alternate paced heart rate during delivery of the extra-systolic stimulation therapy wherein the data set is disposed in, or proximate to, a region of a possibly masked tachycardia rhythm;
comparing the alternate paced heart rate to the correlated heart rate to determine if the alternate paced heart rate is about double or about half of the correlated heart rate; and
in the event that the alternate paced heart rate is about double or one-half of the correlated heart rate, withholding delivery of the extra-systolic stimulation therapy.

16. A method according to claim 15, further comprising:
applying an arrhythmia detection technique; and
in the event that an arrhythmia is detected, attempting to terminate the arrhythmia.

17. A method according to claim 16, wherein attempting to terminate the arrhythmia comprises at least a one of: providing an anti-tachycardia pacing therapy, providing a cardioversion therapy, providing a defibrillation therapy, providing a burst-type pacing therapy, providing a ramp-type pacing therapy.

18. A method for initiating or gradually suspending delivery of an extra-systolic stimulation cardiac pacing therapy, comprising:
sensing electrical activity of a heart to provide a heart rate signal for said heart;
correlating the heart rate signal and an extra-systolic interval for an extra-systolic stimulation therapy to a therapy initiation-and-suspension table containing at least a plurality of heart rates and a plurality of extra-systolic intervals; and
based on a mapped location of the heart rate signal on the table and a corresponding extra-systolic interval either delivering, or inhibiting delivery of, the extra extra-systolic stimulation therapy, wherein the therapy initiation-and-suspension table includes a plurality of therapy transition rules,
wherein one therapy transition rule provides a series of relatively long extra-systolic intervals compared to a cardiac cycle interval for a short period of time following initial delivery of the extra-systolic stimulation therapy and wherein said intervals are progressively shortened as the heart rate decreases during delivery of the extra-systolic stimulation therapy, or
wherein delivery of the extra-systolic stimulation therapy may not be suspended immediately in the event that the heart rate exceeds a pre-established heart rate limit, wherein the table includes evoked response information, said information derived from measurements of an evoked response from the extra-systolic stimulation therapy, said information establishing, for at least one cardiac cycle, a refractory period of the chamber of the heart, and
wherein said information comprises at least a one of: an evoked R-wave response, an evoked R-wave timing parameter, an evoked R-wave morphology characteristic, an evoked P-wave response, an evoked P-wave timing parameter, an evoked P-wave morphology characteristic, an evoked T-wave response, an evoked T-wave timing parameter, an evoked T-wave morphology characteristic, a ventricular pressure signal, an atrial pressure signal, a change of magnitude of a maximum derivative of the ventricular pressure signal, a change of magnitude of a maximum derivative of the atrial pressure signal.

19. A method according to claim 18, wherein the table includes empiric heart rate-based rules for refractory period changes of a chamber of the heart for a plurality of heart rates.

20. A method according to claim 18, wherein in the event that the heart comprises a part of a chronotropically incompetent hemodynamic system reducing a rate responsiveness characteristic relative to a detected patient activity signal, so that the resulting rate response slope for a chronotropically incompetent hemodynamic system reflects a wider range of enhanced hemodynamic function over a wider range of heart rates.

21. A computer readable medium for causing a programmable processor to perform a method of delivering or withholding delivery of an extra-systolic stimulation therapy, comprising:
instructions for sensing electrical activity of a heart to provide a heart rate signal for said heart;
instructions for mapping the heart rate signal and an extra-systolic interval for an extra-systolic stimulation therapy to a table containing at least a plurality of heart rates and a plurality of extra-systolic intervals; and
based on the location on the table of the mapped heart rate signal and the mapped extra-systolic interval either instructions for delivering, or inhibiting delivery of, the extra extra-systolic stimulation therapy,
wherein the table includes evoked response information, said information derived from measurements of an evoked response from the extra-systolic stimulation therapy, said information establishing, for at least one cardiac cycle, a refractory period of the chamber of the heart,
wherein the table includes empiric heart rate-based rules for refractory period changes of a chamber of the heart for a plurality of heart rates, and
wherein said information comprises at least a one of: an evoked R-wave response, an evoked R-wave timing parameter, an evoked R-wave morphology characteristic, an evoked P-wave response, an evoked P-wave timing parameter, an evoked P-wave morphology characteristic, an evoked T-wave response, an evoked T-wave timing parameter, an evoked T-wave morphology characteristic, a ventricular pressure signal, an atrial pressure signal, a change of magnitude of a maximum derivative of the ventricular pressure signal, a change of magnitude of a maximum derivative of the atrial pressure signal.

22. A medium according to claim 21, wherein at least some of said plurality of mapped heart rates and extra-systolic intervals incorporate reduced extra-systolic intervals in the event that the heart rate increases.

23. A medium according to claim 21, wherein at least some of said plurality of mapped heart rates and extra-systolic intervals incorporate increased extra-systolic intervals in the event that the heart rate decreases.

24. A medium according to claim 22, wherein said mapped heart rates and extra-systolic intervals incorporate a security-timing margin for a tachycardia induction portion of the table.

25. A medium according to claim 21, wherein at least a portion of the mapped location of the table incorporates information regarding a predicted degree or a measured degree of a stroke volume augmentation resulting from the extra-systolic stimulation therapy.

26. A medium according to claim 21, wherein at least a portion of the mapped locations of the table incorporates information regarding enhanced arrhythmia detection.

27. A medium according to claim 26, wherein in the event that the portion of the mapped locations of the table include potential for a masked tachycardia rhythm, executing one of instructions for periodically withholding delivery of the extra-systolic stimulation therapy and instructions for decreasing the extra-systolic interval.

28. A system for delivering or withholding delivery of an extra-systolic stimulation cardiac pacing therapy, comprising:
    means for sensing electrical activity of a heart to provide a heart rate signal for said heart;
    means for correlating the heart rate signal and an extra-systolic interval for an extra-systolic stimulation therapy to a data set having at least a plurality of heart rates and a plurality of extra-systolic intervals; and
    means for one of delivering or inhibiting delivery of the extra extra-systolic stimulation therapy
    based on the correlated heart rate signal,
    wherein the data set includes evoked response information, said response information derived from measurements of an evoked response from the extra-systolic stimulation therapy, said response information establishing, for at least one cardiac cycle, a refractory period of the chamber of the heart, and
    wherein said response information comprises at least one of: an evoked R-wave response, an evoked R-wave timing parameter, an evoked R-wave morphology characteristic, an evoked P-wave response, an evoked P-wave timing parameter, an evoked P-wave morphology characteristic, an evoked T-wave response, an evoked T-wave timing parameter, an evoked T-wave morphology characteristic, a ventricular pressure signal, an atrial pressure signal, a change of magnitude of a maximum derivative of the ventricular pressure signal, a change of magnitude of a maximum derivative of the atrial pressure signal.

29. A system according to claim 28, wherein the data set includes empiric heart rate-based guidance for refractory period changes of a chamber of the heart for a plurality of heart rates.

30. A system according to claim 28, wherein said correlated heart rate signal and said plurality of extra-systolic intervals incorporate reduced extra-systolic intervals for a set of relatively higher heart rates.

31. A system according to claim 28, wherein said correlated heart rate signal and said plurality of extra-systolic intervals incorporate increased extra-systolic intervals for a set of relatively lower heart rates.

32. A system according to claim 28, wherein said correlated heart rate signal and said plurality of extrasystolic intervals incorporate a security-timing margin for a tachycardia induction portion of the data set.

33. A system according to claim 28, wherein the data sets incorporates information regarding one of a predicted degree and a measured degree of a stroke volume augmentation value.

34. A system according to claim 28, wherein the data set incorporates information regarding enhanced arrhythmia detection.

35. A system according to claim 34, wherein the data set includes potential for a masked tachycardia rhythm, and further comprising:
    means for one of periodically withholding delivery of the extra-systolic stimulation therapy and decreasing the extra-systolic interval.

36. A system according to claim 34, further comprising:
    means for intermittently withholding delivery of the extra-systolic stimulation therapy for at least one cardiac cycle for every N cardiac cycles to expose a masked tachycardia rhythms, wherein N comprises a non-zero integer.

37. A system according to claim 34, wherein the information regarding enhanced arrhythmia detection includes a reduced electrogram blanking period following delivery of a cardiac pacing stimulation pulse or an extra-systolic stimulation pulse.

38. A system according to claim 37, wherein the reduced electrogram blanking period includes one of a cross-chamber blanking period and a same-chamber blanking period.

39. A system according to claim 37, wherein the reduced electrogram blanking period extends at least one arrhythmia sensing interval for at least a portion of relatively higher heart rates.

40. A system according to claim 28, wherein the data set incorporates information regarding a diastolic compromise condition.

41. A system according to claim 28, further comprising:
    for a plurality of relatively low heart rates, means for delivering the extra-systolic stimulation therapy for every cardiac cycle; and for a plurality of relatively high heart rates, means for withholding delivery of the extra-systolic stimulation therapy.

42. A system according to claim 41, further comprising:
    means for applying an alternate paced heart rate during delivery of the extra-systolic stimulation therapy wherein the data set is disposed in, or proximate to, a region of a possibly masked tachycardia rhythm;
    means for comparing the alternate paced heart rate to the correlated heart rate signal to determine if the alternate paced heart rate is one of about double and about half of the correlated heart rate; and in the event that the alternate paced heart rate is about double or one-half of the correlated heart rate signal, means for withholding delivery of the extra-systolic stimulation therapy.

43. A system according to claim 42, further comprising:

means for applying an arrhythmia detection technique; and means for attempting to terminate an arrhythmia detected by the means for applying.

44. A system according to claim 43, wherein the means for attempting to terminate the arrhythmia comprises at least a one of:

means for providing an anti-tachycardia pacing therapy, means for providing a cardioversion therapy, means for providing a defibrillation therapy, means for providing a burst-type pacing therapy, means for providing a ramp-type pacing therapy.

* * * * *